United States Patent [19]

Mowbray et al.

[11] Patent Number: 5,783,572
[45] Date of Patent: Jul. 21, 1998

[54] QUINOXALINEDIONE NMDA RECEPTOR ANTAGONISTS

[75] Inventors: Charles Eric Mowbray; Alan Stobie; Michael Jonathan Fray; David John Bull; Christopher Lee Carr, all of Sandwich, United Kingdom

[73] Assignee: Pfizer Inc., New York, N.Y.

[21] Appl. No.: 793,896

[22] PCT Filed: Sep. 1, 1995

[86] PCT No.: PCT/EP95/03483

§ 371 Date: Mar. 12, 1997

§ 102(e) Date: Mar. 12, 1997

[87] PCT Pub. No.: WO96/08485

PCT Pub. Date: Mar. 21, 1996

[30] Foreign Application Priority Data

Sep. 13, 1994 [GB] United Kingdom ............... 9418443

[51] Int. Cl.$^6$ ............... A61K 31/55; A61K 31/495; C07D 403/06
[52] U.S. Cl. ............... 514/212; 514/234.8; 514/249; 540/599; 544/116; 544/354
[58] Field of Search ............... 544/354, 116; 514/249, 212, 234.8; 540/599

[56] References Cited

U.S. PATENT DOCUMENTS 5,028,606 7/1991 Venet et al. ............... 514/249

FOREIGN PATENT DOCUMENTS

| 260744 | 3/1988 | European Pat. Off. |
| 377112 | 7/1990 | European Pat. Off. |
| 572852 | 12/1993 | European Pat. Off. |
| 9400124 | 1/1994 | WIPO |

OTHER PUBLICATIONS

Doble, *Therapie* 50, pp. 319–337 (1995).
Kornberg et al, *Chemical Abstracts* vol. 126, No. 131475 (Abstract for WO 96 40650 Dec. 19, 1996), 1997.
Acklin et al, *Chemical Abstracts* vol. 126, No. 251169 (Abstract for WO 97 08155 Mar. 6, 1997).

*Primary Examiner*—Emily Bernhardt
*Attorney, Agent, or Firm*—Peter C. Richardson; Paul H. Ginsburg

[57] ABSTRACT

Compounds of formula (I):

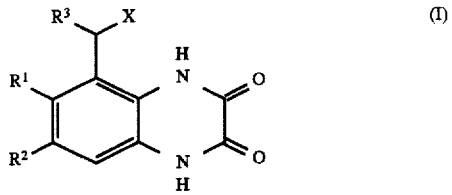

and their pharmaceutically acceptable salts, wherein $R^1$ and $R_2$ are each independently Cl, Br, $CH_3$, $CH_2CH_3$ or $CF_3$; $R^3$ is H, $CH_3$ or $CH_2CH_3$; and X is a 5-membered heterocyclic group containing up to four nitrogen atoms, attached via a nitrogen atom, the said group being optionally substituted by $C_1$–$C_6$ alkyl or $(CH_2)_n NR^4 R^5$, wherein n is an integer from 1 to 5 and $R^4$ and $R^5$ are each independently H, $C_1$–$C_6$ alkyl, $C_3$–$C_6$ cycloalkyl or $C_1$–$C_4$ alkyl substituted by phenyl or pyridyl, or $R^4$ and $R^5$ are linked to form, together with the nitrogen atom to which attached, a pyrrolidine, piperidine, piperazine, N-($C_1$–$C_4$ alkyl) piperazine, morpholine or azepine group, or, when X is triazolyl, said group may optionally be benzofused, are NMDA antagonists of value in the treatment of acute neurodegenerative disorders, e.g. arising from stroke or traumatic head injury and in chronic neurological disorders, e.g. senile dementia and Alzheimer's disease.

7 Claims, No Drawings

QUINOXALINEDIONE NMDA RECEPTOR ANTAGONISTS

This invention relates to derivatives of 1,4-diydroqainoxalin-2,3-dione which are selective antagonists of N-methyl-D-aspartate receptors.

BACKGROUND OF THE INVENTION

L-Glutamic acid is an excitatory amino acid neurotransmitter whose physiological role in the brain involves interaction with four receptors, three of which are named after the selective agonists NMDA (N-methyl-D-aspartate), AMPA (2-amino-3-hydroxy-5-methyl-4-isoxazolepropionic acid) and kainate. The fourth receptor is termed the metabotropic receptor. In addition to a binding site for glutamic acid, the NMDA receptor possesses high affinity binding sites for dissociative anaesthetics (e.g. ketamine), polyamines (e.g. speimine), glycine and certain metal ions (e.g. $Mg^{2+}$, $Zn^{2+}$). Since the NMDA receptor has an absolute requirement to bind glycine for activation to occur, glycine antagonists can act as functional NMDA antagonists.

In the region of a cerebral infarct, anoxia for example, causes abnormally high concentrations of glutaric acid to be released, which lead to an over-stimulation of NMDA receptors, resulting in the degeneration and death of neurones. Thus, NMDA receptor antagonists, which have been shown to block the neurotoxic effects of glutamic acid in vitro and in vivo, may be useful in the treatment and/or prevention of any pathological condition in which NMDA receptor activation is thought to be important. Examples of such conditions include acute neurodegenerative disorders arsing from events such as stroke, transient ischaemic attack, peri-perative ischaemia and traumatic head injury to the brain or spinal cord. In addition NMDA antagonists may be of use in treating certain chronic neurological disorders such as senile dementia and Alzheimer's disease. They may also have utility in conditions in which peripheral nerve function has been impaired such as retinal and macular degeneration.

Furthermore, NMDA antagonists have been shown to possess anti-convlsant and anxiolytic activity and may therefore be used to treat epilepsy and axiety. NMDA antagonists may attenuate the effects of alcohol withdrawl from physically dependent animals (K. A. Grant et al. J. Pharm. Exp. Ther. (1992), 260, 1017) and thus NMDA antazonists may be of use in the treatment of alcohol addiction and pain.

Various derivatives of 1,2,3,4-tetrahydroquinaline-2,4-dione have been described as NMDA (glycine site) rector antagonists (see EP-A0459561 and EP-A-0431676) while WO 91/013873 and JO 322-0124 describe 1,4-dihydroquinoxaline-2,3-diones as glutamic acid antagonists. WO 94/00124 describes 1,4-dihydroquinoxaline-2,3-diones having high affinity for the glycine binding site with utility for Long stroke and red disorders.

EP-A-0377112 and EP-A-0572852 describe various quinoxaline -2,3-diones having CNS activity while EP-A-0260744 describes 1H-imidazol-1-yl-methyl-benzimidazole derivatives useful for treating androgenic hormone disorders. Chemical Abstracts no. 184281, 117(19), 1992 describes structure activity relationships and the physiological implications of NMDA inhibition of a number of quinoxaline derivatives.

SUMMARY OF THE INVENTION

The compounds of the present invention are not only highly potent antagonists of the NOMA (glycine site) receptor but are also highly selective having little or no affinity for the ABA receptor.

Thus the present invention provides compounds having the formula:

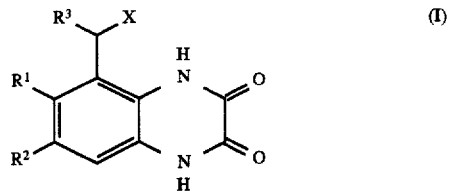

and their pharmaceutically acceptable salts, wherein $R^1$ and $R^2$ are each independently Cl, Br, $CH_3$, $CH_2CH_3$ or $CF_3$; $R^3$ is H, $CH_3$ or $CH_2CH_3$; and X is a 5-membered heterocyclic group containing up to four nitrogen atoms, attached via a nitrogen atom, the said group being optionally substituted by $C_1$–$C_6$ alkyl or $(CH_2)_n NR^4R^5$, wherein n is an integer from 1 to 5 and $R^4$ and $R^5$ are each independently H, $C_1$–$C_6$ alkyl, $C_3$–$C_6$ cycloalkyl or $C_1$–$C_4$ alkyl substituted by phenyl or pyridyl, or $R^4$ and $R^5$ are linked to form, together with the nitrogen atom to which they are attached, a pyrrolidine, piperidine, piperazine, N-($C_1$–$C_4$ alkyl) piperazine, morpholine or azepine group, or, when X is triazolyl, said group may optionally be benzo-fused.

In the above definitions all alkyl groups containing three or more carbon atoms may be straight or branched-chain. Particular examples of the heterocyclic group X include imidazolyl, pyrazolyl, 1,2,4-triazolyl, tetrazolyl, 1,2,3-triazolyl and benzotriazolyl, each being optionally substituted as defined above. Compounds of the invention containing an acidic or basic group are capable of forming acid or base addition salts, and these salts, when pharmaceutically acceptable, are within the scope of the invention. In some instances the compounds may exist as tautomers and all such tautomers are included within the scope of the invention, whether separated or not. In addition compounds containing asymmetric centres can exist as enantiomers and diastereoisomers, and the invention includes the separated individual isomers as well as mixtures of isomers.

In preferred compounds, $R^1$ and $R^2$ are both Cl and $R^3$ is preferably $CH_2CH_3$. X is preferably 1,2,3-triazol-1-yl, benzotrazol-1-yl, or 1,2,4-triazol-4-yl. A particular and preferred compound is 6,7-dichloro-1,4-dihydro-5-[1-(1,2,4-triazol-4-yl)-prop-1-yl-quinoxnal-2,3-dione.

DETAILED DESCRIPTION OF THE INVENTION

The compounds of formula (I) may be prepared from the corresponding 2,3-dimethoxy-quinoxaline derivative of formula (II) by the following route wherein hal is chloro or bromo. In this route the 2,3-dione functionality is masked as the dimethoxy derivative during the reaction sequence and this is only removed at the final stage-:

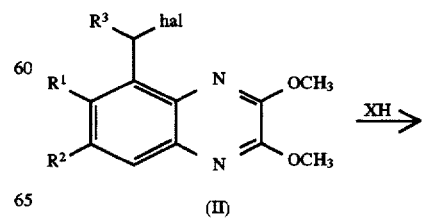

-continued

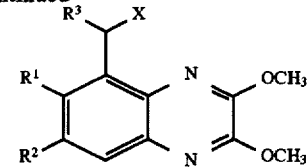

(III)

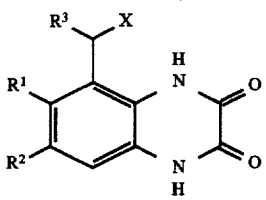

The reaction of the halo derivative of formula (II) and the desired heterocyclic compound of formula XH is achieved in a conventional manner, either by heating the reactants with or without an organic solvent (e.g. tetrahydrofuran or dimethylacetamide), optionally in the presence of an acid scavenger (e.g. potassium carbonate) or by reaction of the heterocyclic compound with sodium hydride to generate the appropriate anion prior to addition of the compound of formula (II). Conversion of the dimethoxy derivative (III) to give the product of formula (I) is typically achieved by refluxing in a mixture of an organic solvent (e.g dioxane) and dilute hydrochloric acid for a period of 2 to 8 hours. The product is isolated by conventional procedures.

In some instances elaboration of the heterocyclic group X can take place after attachment to the quinoxaline ring. Thus for example, the reaction can be performed with a heterocyclic compound bearing a chloroalkyl substituent to yield the corresponding compound of formula (I). This can then be reacted with an amine of formula $R^4R^5NH$ followed by the hydrolysis step to provide the compound of formula (I) wherein the heterocyclic group is substituted by $(CH_2)_nNR^4R^5$. Other variants of this procedure will be evident to those skilled in the art.

Appropriate reaction conditions and reagents for the above reactions can be determined by routine investigation and by reference to the experimental examples included herewith.

The starting materials of formula (II) can in some instances be prepared from known 1,4-dihydroquinoxalinedione derivatives while in other cases they must be synthesised via the appropriate diaminobenzene derivative. Thus, for example, in the case of the compound of formula (II) wherein $R^3$ is methyl, the required 5-(1-bromoethyl) derivative may be prepared via the 2,3-dimethoxy-5-amino derivative (IV) wherein $R^1$ and $R^2$ are as previously defined.

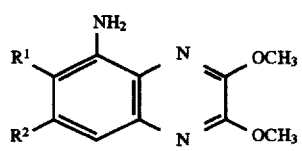

(IV)

The route is illustrated for the case where $R^1$ and $R^2$ are both halo-:

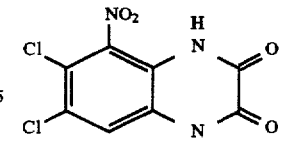

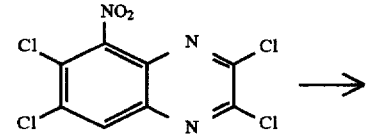

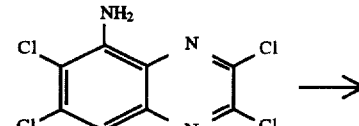

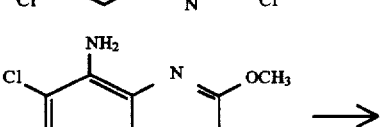

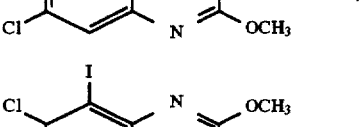

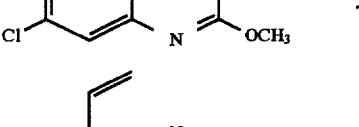

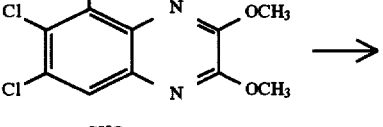

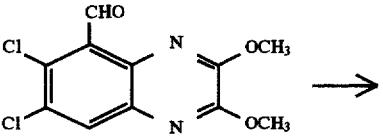

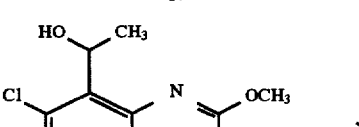

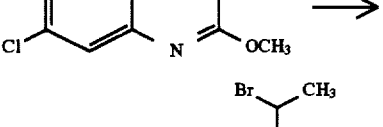

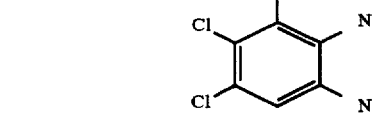

The process involves, first reaction with thionyl chloride to give the 5-nitro-2,3,6,7-tetrachloroquinoxaline which is then reduced using tin (II) chloride to the 5-amino derivative and then reacted with sodium methoxide to yield the 2,3-dimethoxy derivative. The product is reacted in turn with sodium nitrite and potassium iodide to give the 5-iodo product which is reacted with tributylvinylstannane under palladium catalysis followed by oxidation with ozone to give the 5-formyl derivative. This is reacted with methylmagnesium bromide and the resulting 5-(1-hydroxyethyl) product reacted with triphenylphosphine and carbon tetrabromide to yield the required 5-(1-bromoethyl) intermediate. The intermediate of formula (II) wherein $R^1$ and $R^2$ are both halo and wherein $R^3$ is ethlyl is prepared in a similar mainner from the 5-formyl derivative using ethyl magnesium bromide followed by conversion to the 5-(1-bromopropyl) intermediate, as above.

Alternatively, for compounds of formula (II) wherein $R^1$ and $R^2$ are each chloro, $R^3$ is H and X is bromo, the required 5-bromomethyl derivative may be prepared by the following synthetic route:

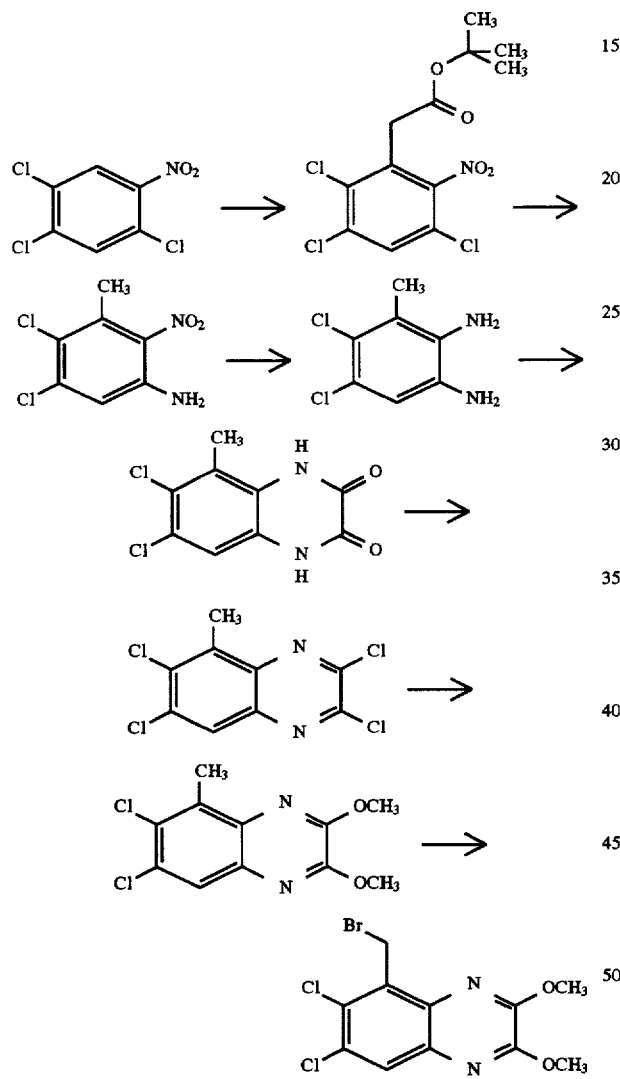

This route starts with 2,4,5-trichloronitrobenzene. A vicarious nucleophilic aromatic substitution reaction using t-butyl chloroacetate and potassium t-butoxide gives t-butyl 2-nitro-(3,5,6-trichlorophenyl)acetate which is treated with ammonia to give the known 3-amino-5,6-dichloro-2-nitrotoluene. Reduction of the nitro group followed by reaction with oxalic acid yields the 5-methyl-1,4-dihydroquinoxalinedione. This is again converted to the 2,3-dimethoxy derivative as previously described, followed by reaction with N-bromosuccinimide and α,α-azoisobutyronitrile to give the desired 5-bromomethyl intermediate.

A different process is utilised in the case of the compound of formula (II) wherein $R^1$ and $R^2$ are both methyl, $R^3$ is H and hal is chloro-:

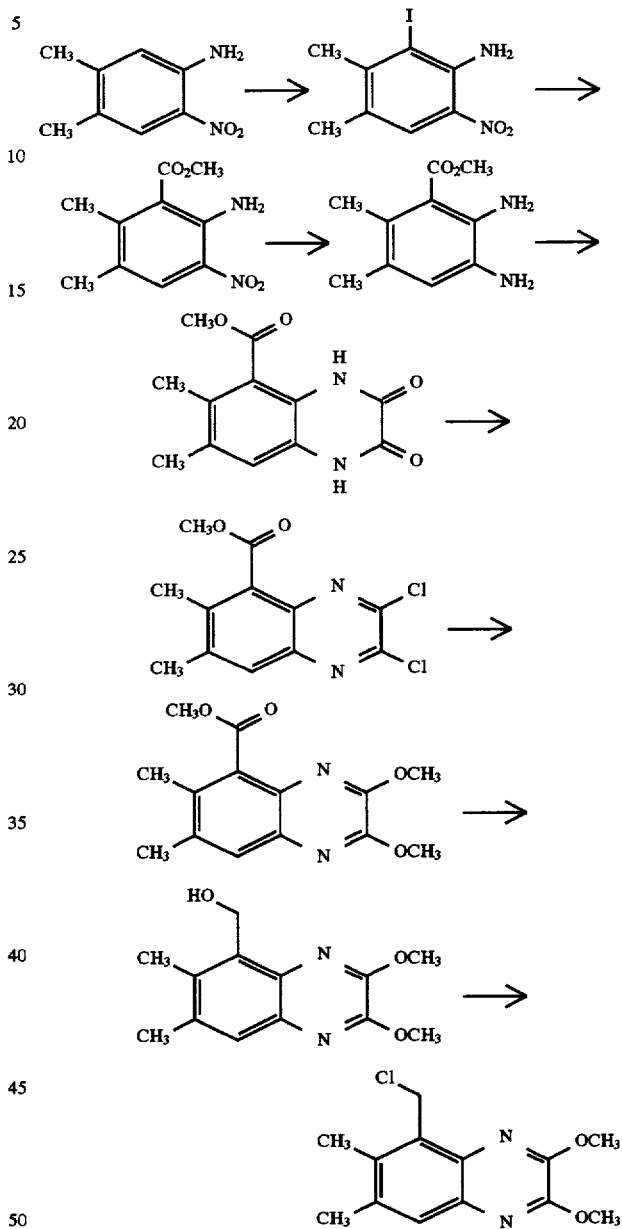

In this process 4,5-dimethyl-2-nitroaniline is reacted with silver sulphate and iodine to give the 6-iodo derivative which is reacted with methanol and bis(triphenylphosphine) palladium(II) chloride in the presence of ethyldiisopropylamine under a carbon monoxide atmosphere to give methyl 2-amino-5,6-dimethyl-3-nitrobenzoate. Reduction of the nitro group followed by reaction with oxalic acid gives the 1,4-dihydroquinoxalinedione which is converted to the 2,3-dimethoxy derivative as before. Finally, reduction using diisobutylaluminium hydride gives the 5-hydroxymethyl derivative which is converted to the required 5-chloromethyl derivative by reacting with thionyl chloride.

Appropriate reagents and conditions for each of the above steps may readily be determined by reference to literature precedents and to the preparative details given hereafter. Alternatives and variations will be evident to persons skilled in the art to enable all the compounds defined by formula (I) to be prepared.

The heterocyclic compounds of formula X-H are generally known compounds, or where not described in the literature, they can be prepared by conventional procedures following literature precedents. Synthesis of various substituted heterocyclic derivatives are included in the preparative details given hereafter.

The binding affinity of the compounds of the invention for the glycine site of the NMDA receptor may be measured by testing their ability to displace a selective glycine site radioligand from rat brain membranes as described in Brit. J. Pharm. (1991), 104, 74. In a variation of this method, thoroughly washed membrane protein is incubated with [$^3$H]-L-689,560 for 90 minutes using tris-acetate buffer (pH 7.4). Displacement of the radioligand, using a range of test compound concentrations, is used to derive $IC_{50}$ (50% inhibitory concentration) values.

Functional in vitro glycine antagonism is demonstrated by the ability of the compounds to inhibit the depolarizations in rat cortical slices induced by NMDA, similar to the method described in J. Med. Chem., (1990), 33, 789 and Brit. J. Pharm. (1985), 84, 381. In a variation of the procedure, the response to a standard concentration of NMDA is measured in the presence of a range of test compound concentrations, and the results obtained are used to derive $EC_{50}$ (50% effective concentration) values.

The binding affinity of the compounds of the invention for the AMPA receptor may be measured by testing their ability to displace the radioligand [$^3$H]-AMPA from rat brain membranes. Membrane homogenate is incubated with radioligand (10 nM) in the presence or absence of test compounds at various concentrations at 4° C. for 45 minutes. Free and bound radiolable are separated by rapid filtration, and radioactivity is measured by liquid scintillation counting. All compounds tested failed to displace more than 50% of the bound radioligand, at a concentration of 10μM demonstrating the high selectivity of the compounds of the invention.

The compounds of formula (I) may be adminstered to a subject in need of treatment by a variety of conventional routes of administration, including oral and intravenous administration. The compounds have potential for absorption through the gastrointestinal tract and thus administration by slow release formulations is also possible.

In general, a therapeutically-effective oral dose of the active compounds of formula (I) is likely to range from 0.1 to 100 mg/kg body weight of the subject to be treated, preferably 1 to 10 mg/kg, and an intravenous dose is likely to range from 0.01–10mg/kg body weight of subject treated, preferably 0.1–5 mg/kg. Where necessary, the active compounds may also be administered by intravenous infusion, at a dose which is likely to range from 0.01–1 mg/kg/hr. In practice the physician will determine the actual dosage which will be most suitable for an individual patient and it will vary with age, weight and response of the particular patient. The above dosages are exemplary of the average case but there can, of course, be individual instances where higher of lower dosages ranges are merited, and such are within the scope of this invention.

Although the compounds of formula (I) can be administered alone, they will generally be administered in admixture with a pharmaceutical carrier selected with regard to the intended route of administration and standard pharmaceutical practice. For example, oral administration may be in the form of tablets containing such excipients as starch or lactose, in capsules either alone or in admixture with excipients, or in the form of elixirs or suspensions containing flavouring or colouring agents. The compounds may be injected parenterally, for example intravenously, intramuscularly or subcutaneously. For parenteral administration they are best used in the form of a sterile aqueous solution of an appropriate salt of the compound and the solution may contain other substances such as salts to make it isotonic with blood.

Thus, in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament.

The invention further includes the use of a compound of the formula (I), or of a pharmaceutically acceptable salt thereof, for the manufacture of a medicament for the treatment or prophylaxis of any of the conditions mentioned above.

Preparation of compounds according to the invention is illustrated by the following Examples. Intermediate compounds may be made as described in the following Preparations.

EXPERIMENTAL EXAMPLES

GENERAL

Melting points were determined using a Buchi apparatus in glass capilliary tubes and are uncorrected. Spectroscopic data were recorded on Perkin-Elmer 983 (Infra Red), Fisons Trio 1000 (Mass Spectrometer, thermospray using ammonium acetate in aqueous methanol as carrier), and Bruker AC300 and Varian Unity 300 NMR instruments (both 300 Mz), and were consistent with the assigned structures. Column chromatography was accomplished on Kieselgel 60, (230–400 mesh) from E. Merck, Darmstadt. Kieselgel 60 $F_{254}$ plates from E. Merck were used for thin layer chromatography (TLC), and compounds were visualized with UV light or chloroplatinic acid/potassium iodide solution. In cases where compounds analyzed as hydrates, the presence of water was evident in the enhanced peak due to water in the proton NMR spectra. The purity of compounds was carefully assessed using analytical TLC and proton NMR (300 MHz), and the latter technique was used to calculate the amount of solvent in solvated samples. In multistep sequences, the purity and structure of intermediates were verified spectroscopically by proton NMR. Proton NMR shifts are quoted in parts per million downfield from tetramethylsilane.

Example 1

1,4-Dihydro-6,7-dichloro-5-(1,2,4-triazol-1-ylmethyl)quinoxalin-2,3-dione (a) A mixture of 5-bromomethyl-6,7-dichloro-2,3-diethoxyquinoxaline (Preparation 1,176 mg, 0.5 mmol), 1,2,4-triazole (69 mg, 1.0 mmol) and anhydrous potassium carbonate (138 mg, 1.0 mmol) in dry N,N-dimethylacetamide (2 mL) was heated at 50° C. with stirring for 18 hours. The mixture was diluted with ethyl acetate, washed with water, and concentrated under reduced pressure. The residue was purified by flash chromatography using a hexane:ethyl acetate:methanol gradient to give 6,7-dichloro-2,3-dimethoxy-5-(1,2,4-triazol-1-ylmethyl) quinoxaline (99 mg, 58%).

$^1$H NMR (300 MHz, CDCl$_3$) 4.15 (6H, s), 6.05 (2H, s), 7.85 (1H, s), 7.95 (1H, s), 8.10 (1H, s). m/z (thermospray) 340 (MH$^+$).

(b) 6,7-Dichloro-2,3-dimethoxy-5-(1,2,4-triazol-1-ylmethyl)-quinoxaline (99 mg, 0.29 mmol) was heated in a mixture of 2M hydrochloric acid (2 mL) and dioxane (2 mL) at reflux for 3 hours. The solvent was removed under reduced pressure and the solid residue was suspended in water and filtered to give 1,4-dihydro-6,7dichloro-5-(1,2,4-triazol-1-ylmethyl)-quinoxalin-2,3-dione (60 mg, 62%) as a white solid, mp>320° C. Found: C, 39.47; H 2.49; N, 20.54. $C_{11}H_7Cl_2N_5O_2 \cdot 1.25 \cdot H_2O$ requires C, 39.48; H 2.86; N, 20.93%.

$^1$H NMR (300 MHz, DMSO-$d_6$) 5.80 (2H, s), 7.22 (1H, s), 7.95 (1H, s), 8.45 (1H, s), 11.79 (1H, br s), 12.15 (1H, s).

Examples 2–11

The compounds shown in Table 1 below were prepared by the method of Example 1, starting with the appropriate heterocycle instead of 1,2,4-triazole. Examples 4 to 11 were prepared using tetrahydrofuran as the solvent in step (a), heating under reflux for a period of between 2 and 24 hours.

TABLE 1

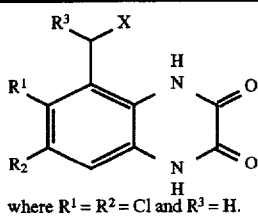

where $R^1 = R^2 = Cl$ and $R^3 = H$.

| Example | X | mp (°C.) | Formula | Conditions step (a) (Yield) | Yield (b) | Analysis: Found (Requires) C | H | N |
|---|---|---|---|---|---|---|---|---|
| 2 | (pyrazol-1-yl) | >320 | $C_{12}H_8Cl_2N_4O_2 \cdot 0.75H_2O$ | As Ex 1 (69%) | 95% | 44.40 (44.60 | 2.95 2.78 | 17.26 17.03) |
| 3 | (imidazol-1-yl) | 315–316 (dec) | $C_{12}H_8Cl_2N_4O_2$ | As Ex 1 (68%) | 95% | Note 1 | | |
| 4 | (1,2,3-triazol-1-yl) | 323–325 (dec) | $C_{11}H_7Cl_2N_5O_2 \cdot HCl \cdot 0.5H_2O$ | $K_2CO_3$, tetrahydrofuran, reflux 2 h (36%) | 73% | 37.20 (36.95 | 2.24 2.54 | 19.70 19.59) |
| 5 | (benzotriazol-1-yl) | 314–316 (dec) | $C_{15}H_9Cl_2N_5O_2 \cdot H_2O$ | As Ex 4 (19%) | 45% | 47.39 (47.03 | 2.92 2.85 | 18.42 18.04) |
| 6 | (methylimidazolyl, ratio 4:1) | — | $C_{13}H_{10}Cl_2N_4O_2 \cdot HCl \cdot H_2O$ | As Ex 4, reflux 18 h (40%) | 99% | 41.03 (41.13 | 3.28 3.45 | 14.39 14.76) |
| 7 | DELETED | | | | | | | |
| 8 | (phenylimidazolyl) | >300 | $C_{18}H_{12}Cl_2N_4O_2 \cdot HCl$ | As Ex 4, reflux 24 h (17%) | 72% | 51.24 (51.03 note 3 | 2.85 3.09 | 12.57 13.22) |
| 9 | (methyltriazolyl) note 4 | >320 | $C_{12}H_9Cl_2N_5O_2 \cdot HCl$ | As Ex 4, reflux 18 h (33%) | 56% | 39.30 (39.75 | 2.70 2.78 | 19.19 19.31) |

TABLE 1-continued where $R^1 = R^2 = Cl$ and $R^3 = H$.

| Example | X | mp (°C.) | Formula | Conditions step (a) (Yield) | Yield (b) | Analysis: Found (Requires) C | H | N |
|---|---|---|---|---|---|---|---|---|
| 10 | [triazole with CH₃] note 4 | 302–304 (dec) | $C_{12}H_9Cl_2N_5O_2 \cdot HCl \cdot H_2O$ | As Ex 4, reflux 18 h (23%) | 40% | 37.94 (37.87 | 3.10 3.18 | 18.36 18.40) |
| 11 | [triazole with CH₂CH₃] note 5 | 300–302 (dec) | $C_{13}H_{11}Cl_2N_5O_2 \cdot HCl$ | As Ex 4, reflux 18 h (15%) | 64% | 41.33 (41.46 | 3.22 3.21 | 18.78 18.59) |

Notes to Table 1
1. $^1$H NMR (300 MHz, DMSO-d$_6$) 5.74 (2H, s), 7.47 (1H, s), 7.68 (1H, s) 7.73 (1H, s), 9.06 (1H, s) 11.96 (1H, br s), 12.34 (1H, br s), 14.86 (1H, br s). m/z (thermospray) 311 (MH$^+$).
2. $^1$H NMR (300 MHz, DMSO-d$_6$) 5.88 (2H, s), 7.48 (1H, s), 7.60 (2H, m), 7.85 (1H, dd, J 6 and 2 Hz), 8.02 (1H, d J 8 Hz), 9.03 (1H, s), 11.96 (1H, br s), 12.27 (1H, br s). m/z (thermospray) 361 (MH$^+$).
3. $^1$H NMR (300 MHz, DMSO-d$_6$) 5.72 (2H, s), 7.36 (1H, m), 7.45 (2H, m), 7.75 (2H, d J 8 Hz), 7.83 (1H, s), 8.82 (1H, br s), 11.96 (1H, br s), 12.14 (1H, br s).
4. The reaction of 2-methyl-1,2,4-triazole gave two isomers which were separated by column chromatography over silica gel (20–40μ) (gradient elution with ethyl acetate/hexane) after step (a). The structures were assigned using Rotating Frame Overhauser Enhancement Spectroscopy (ROESY) and then separately deprotected using hydrochloric acid as described in Example 1 (b).
5. The reaction of 2-ethyl-1,2,4-triazole gave two isomers of which only one could be obtained pure by flash chromatography (silica gel 20–40μ, eluting with toluene:triethylamine = 9:1). The structure of this isomer was assigned by comparison of the $^1$H NMR spectrum with that of the compound from Example 9 (a).

TABLE 2

Formula (1), where $R^1 = R^2 = CH_3$ and $R^3 = H$

| Example | X | m.p. (°C.) | Formula | Conditions step (a) (Yield) | Yield (b) | $^1$H NMR (300 MHz, DMSO-d$_6$) |
|---|---|---|---|---|---|---|
| 12 | [tetrazole structure] | >280 | $C_{12}H_{12}N_6O_2$ | acetone, K$_2$CO$_3$ reflux 18 h (32%) note | 94% | δ = 2.08 (3H, s), 2.20 (3H, s), 6.20 (2H, s), 7.00 (1H, s), 8.90 (1H, s) 11.59 (1H, br s), 11.93 (1H, br s). m/z (thermospray) 290 (MNH$_4^+$), 273 (MH$^+$) |
| 13 | [tetrazole structure] | >280 | $C_{12}H_{12}N_6O_2$ | acetone, K$_2$CO$_3$ reflux 18 h (59%) note | 78% | δ = 2.12 (3H, s), 2.20 (3H, s), 5.89 (2H, s), 7.00 (1H, s), 9.30 (1H, s), 11.58 (1H, kbr s), 11.92 (1H, br s). m/z (thermospray) 290 (MNH$_4^+$), 273 (MH$^+$) | note: Isomers were separated by column chromatography on silica gel (eluting with dichloromethane then dichloromethane:methanol, 99:1)

Example 14

(1'RS)-1,4-Dihydro-6,7-dichloro-5-(1-imidazol-1-ylethyl)quinoxalin-2,3-dione hydrochloride (a) Methanesulphonyl chloride (239 mg, 2.09 mmol) was added to a solution of 6,7-dichloro-2,3-dimethoxy-5-(1-hydroxyethyl)quinoxaline (527 mg, 1.74 mmol) (Preparation 2) and triethylamine (264 mg, 2.61 mmol) in dry dichloromethane (20 mL) at 20° C. The mixture was stirred for 30 minutes, then tetra-n-butyl ammonium chloride (726 mg, 2.61 mmol) was added in portions. After a further 30 minutes at 20° C., brine (20 mL) was added and the organic layer separated. The aqueous layer was extracted with dichloromethane (2×20 mL), and the combined extracts were dried (MgSO$_4$) and concentrated under reduced pressure. Purification by flash chromatography using hexane/dichloromethane (1:1) gave 5-(1-chloroethyl)-6,7-dichloro-2,3-dimethoxyquinoxaline (95 mg, 17%), as a white solid.

¹H NMR (300 MHz, CDCl₃) rotational isomers evident: 2.17 (6H, br s, 2×CH₃), 4.13 (6H, s, 2×CH₃), 4.20 (6H, s, 2×CH₃), 6.10 (1H, br s, CHCH₃), 6.85 (1H, br s, CHCH₃), 7.87 (2H, s, 2×aromatic H). m/z (thermospray) 321 (MH⁺).

(b) A mixture of 5-(1-chloroethyl)-6,7dichloro-2,3-dimethoxyquinoxaline (95 mg, 0.295 mmol), imidazole (22 mg, 0.325 mmol), anhydrous potassium carbonate (45 mg, 0.325 mmol) in dry dimethylformamide (10 mL) was heated under nitrogen at 100° C. for 6 hours, cooled, and partitioned between brine and three portions of ethyl acetate. The combined organic solutions were dried (MgSO₄) and concentrated under reduced pressure. The residue was purified by flash column chromatography (gradient elution with dichloromethane:mehanol) to give 6,7dichloro-2,3-dimethoxy-5-(1-imidazol-1-ylethyl)quinoxaline (60 mg, 58%); as a yellow solid.

¹H NMR (300 MHz, CDCl₃) 2.18 (3H, d, J 7 Hz), 4.00 (3H, s), 4.10 (3H, s), 6.52 (1H, br q, J 7 Hz), 6.89 (1H, s), 6.97 (1H, s), 7.71 (1H, s), 7.90 (1H, s). m/z (thermospray) 353 (MH⁺).

(c) The product from (b) above was heated with 2M hydrochloric acid in dioxane at reflux for 7 hours according to Example 1(b), to give (1'RS)-1,4-dihydro-6,7-dichloro-5-(1-imidazol-1-ylethyl)quinoxalin-2,3-dione hydrochloride (13 mg, 21%) as a pale buff solid, mp>300° C.

¹H NMR (300 MHz, DMSO-d₆) 2.02 (3H, d, J 7 Hz), 6.33 (1H, q, J 7 Hz), 7.45 (1H, s), 7.65 (1H, s), 7.71 (1H, s), 9.26 (1H, s), 11.84 (1H, br s), 12.33 (1H, br s), 14.82 (1H, br s).

Example 15

1,4-Dihydro-5-(imidazol-1-ylmethyl)-6,7-dimethylquioxalin-2,3-dione (a) A mixture of 5-chloromethyl-2,3-dimethoxy-6,7-dimethylquinoxaline (Preparation 3) (60 mg, 0.22 mmol) and imidazole (1.0 g, 14.7 mmol) was heated at 110° C. for 30 minutes, cooled and diluted with water. The resulting suspension was sonicated for 5 minutes at 20° C. and the solid filtered off. The solid was washed with water, and then hexane, affording 5-(imidazol-1-ylmethyl)-2,3-dimethoxy-6,7-dimethyl-quinoxaline (41 mg, 61%) as an off-white solid.

¹H NMR (300 MHz, CDCl₃) 2.32 (3H, s), 2.35 (3H, s), 4.14 (3H, s), 4.15 (3H, s), 5.23 (2H, s), 6.90 (1H, s), 6.98 (1H, s), 7.55 (1H, s), 7.63 (1H, s). m/z (thermospray) 299 (MH⁺).

(b) The compound from (a), above, (37 mg, 0.12 mmol) was heated with hydrochloric acid and dioxane for 5.5 hours, according to the procedure of Example 1(b) to give 1,4-dihydro-5-(imidazol-1-ylmethyl)-6,7-dimethylquinoxalin-2,3-dione hydrochloride (21 mg, 55%), as an off-white solid, mp 287°–289° C.

¹H NMR (300 MHz, DMSO-d₆) 2.14 (3H, s), 2.23 (3H, s), 5.64 (2H, s), 7.06 (1H, s), 7.20 (1H, s), 7.19 (1H, s), 8.90 (1H, s), 11.54 (1H, br s), 11.97 (1H, br s), 14.58 (1H, br s).

Examples 16–24

Examples 16–21 shown in Table 3 below were prepared by the method of Example 15, either by reacting pyrazole, imidazole or 1,2,3-triazole with 5-chloromethyl-2,3-dimethoxy-6,7-dimethylquinoxaline (Preparation 3), 5-(1-bromoethyl)-6,7-dichloro-2,3-dimethoxyquinoxaline (Preparation 4), or 5-(1-bromopropyl)-6,7-dichloro-2,3dimethoxyquinoxaline (Preparation 5), as appropriate. Examples 22 and 23 were prepared by a variation of Example 15, whereby 5-(1-bromopropyl)-6,7-dichloro-2,3-dimethoxyquinoxaline (preparation 5) and 1,2,4-triazole (22 equivalents) were heated together at 140° C. for 30 minutes. The isomeric products so obtained, 6,7-dichloro-2,3-dimethoxy-5-(1-(1,2,4-triazol-1-yl)prop-1-yl)-quinoxaline and 6,7-dichloro-2,3-dimethoxy-5-(1-(1,2,4-triazol-4-yl)-prop-1-yl)quinoxaline were separated by chromatography on silica gel (eluting with a dichloromethane/methanol gradient) prior to hydrolysis of the dimethoxyquinoxaline in step (b). Example 24 was prepared as for Example 23, using 5-bromomethyl-6,7-dichloro-2,3-dimethoxyquinoxaline (Preparation 1) in place of the compound of preparation 5. The desired 1,2,4-triazole isomer was separated by column chromatography on silica gel, prior to hydrolysis of the dimethoxyquinoxaline in step (b).

TABLE 3

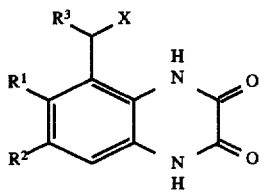

| Example | R¹, R² | R³ | X | mp (°C.) | Formula | Yield (a) | Yield (b) | Analysis: Found (Requires) C | H | N |
|---|---|---|---|---|---|---|---|---|---|---|
| 16 | CH₃ | H | pyrazolyl | 317–319 | C₁₄H₁₄N₄O₂·0.1H₂O | 61% | 62% | 61.76 (61.80 | 5.17 5.26 | 20.57 20.59) |
| 17 | Cl | CH₃ | pyrazolyl | >300 | C₁₃H₁₀Cl₂N₄O₂·0.2H₂O | 55% | 43% | 47.65 (47.49 | 3.03 3.19 | 16.72 17.04) |

TABLE 3-continued

| Example | R¹, R² | R³ | X | mp (°C.) | Formula | Yield (a) | Yield (b) | C | H | N |
|---|---|---|---|---|---|---|---|---|---|---|
| 18 | Cl | $CH_3$ | (pyrazole) | >300 | $C_{12}H_9Cl_2N_5O_2 \cdot 0.5H_2O$ | 65% | 41% | 43.20 (43.20 | 2.70 3.01 | 20.60 20.90) |
| 19 | $CH_3$ | H | (pyrazole) | >300 | $C_{13}H_{13}N_5O_2 \cdot HCl$ | 52% | 55% | | note 1 | |
| 20 | Cl | $CH_2CH_3$ | (pyrazole) | >300 | $C_{14}H_{12}Cl_2N_4O_2 \cdot HCl \cdot 0.75H_2O$ | 70% | 25% | 43.22 (43.21 | 3.47 3.75 | 14.10 14.40) |
| 21 | Cl | $CH_2CH_3$ | (pyrazole) | >300 | $C_{13}H_{11}Cl_2N_5O_2 \cdot 0.3H_2O$ | 32% | 57% | 45.15 (45.18 | 3.28 3.38 | 19.87 20.26) |
| 22 | Cl | $CH_2CH_3$ | (imidazole) | foam | $C_{13}H_{11}Cl_2N_5O_2 \cdot HCl$ | 19% | 55% | | note 2 | |
| 23 | Cl | $CH_2CH_3$ | (imidazole) | 224–226 | $C_{13}H_{11}Cl_2N_5O_2 \cdot HCl \cdot 1.75H_2O$ | 32% | 49% | 38.34 (38.25 | 3.52 3.83 | 17.01 17.16) |
| 24 | Cl | H | (pyrazole) | >300 | $C_{11}H_7Cl_2N_5O_2 \cdot HCl \cdot 0.25H_2O$ | 37% | 81% | 37.25 (37.42 | 2.34 2.43 | 19.83 19.83) |

Notes to Table 3:
1) ¹H NMR (300 MHz, DMSO-$d_6$) 2.13 (3H, s), 2.20 (3H, s), 5.85 (2H, s), 6.99 (1H, s), 7.67 (1H, s), 7.97 (1H, s ), 11.52 (1H, br s), 11.87 (1H, br s).
Note 2: ¹H NMR (300 MHz, DMSO-$d_6$) δ = 0.83 (3H, t, J 6 Hz), 2.43 (2H, m partially obscured by DMSO), 6.36 (1H, t, J 7 Hz), 7.37 (1H, s), 8.10 (1H, s), 8.80 (1H, s), 11.80 (1H, br s), 12.08 (1H, br s). m/z (thermospray) 340 (MH⁺).

Example 25

1,4-Dihydro-6,7-dichloro-5-{4-[3-(4-morpholinyl) propyl]pyrazol-1-ylmethyl}quinoxalin-2,3-dione hydrochloride (a) 4-[3-(4-Morpholinyl)propyl]pyrazole dihydrochloride (268 mg, 1 mmol) was added to a stirred suspension of sodium hydride (120 mg, 80% oil dispersion, 4 mmol) at 0° C. under nitrogen. After 30 minutes, the mixture was cooled to −40° C. and 5-bromomethyl-6,7-dichloro-2,3-dimethoxyquinoxaline (Preparation 1, 235 mg, 0.67 mmol) was added. The mixture was allowed to warm to −20° C. over 1 hour and saturated aqueous ammonium chloride (20 mL) was added. The mixure was diluted with water (100 mL) and extracted with ethyl acetate (2×100 mL). The extracts were washed with water, dried ($MgSO_4$) and concentrated under reduced pressure. The residue was purified by flash chromatography eluting with dichloromethane, then ethyl acetate then finally ethyl acetate:methanol:triethylamine (100:3:1) to give 6,7-dichloro-2,3-dimethoxy-5-{4-[3-(4-morpholinyl)propyl]pyrazol-1-ylmethyl}quinoxaline (278 mg, 89%) as a colourless gum.

¹H NMR (300 MHz, $CDCl_3$) 1.65 (2H, m), 2.26 (2H, t, J 6 Hz), 2.40 (6H, m), 3.62 (4H, m), 4.15 (6H, s), 5.94 (2H, s), 7.14 (1H, s), 7.28 (1H, s), 7.92 (1H, s). m/z (thermospray) 466 (MH⁺).

(b) The quinoxaline from (a) above (276 mg, 0.59 mmol) was heated in a mixture of 2M hydrochloric acid (5 mL) and dioxane (5 mL) at reflux for 6 hours. The mixture was concentrated under reduced pressure and acetone (10 mL) was added. The resulting solid was filtered off and dried under vacuum to give the title compound as a white solid (254 mg, 88%). mp 295°–300° C. (dec). Found C, 46.90; H, 4.83; N, 14.49;

$C_{19}H_{21}Cl_2N_5O_3 \cdot HCl \cdot 0.75H_2O$ requires C, 46.74; H, 4.85; N, 14.34%

Examples 25–42

Examples 26–42, shown in Table 4, were prepared by the method of Example 25, starting with the appropriate 4-substituted pyrazole (Preparations 6–23).

TABLE 4

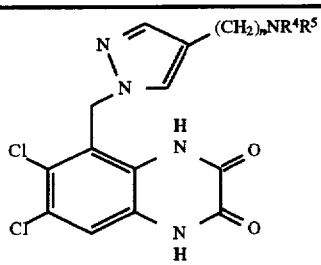

| Example | n | R⁴ | R⁵ | mp (°C.) | Formula | Analysis: Found (Required) C | H | N | Yield (a) | Yield (b) |
|---|---|---|---|---|---|---|---|---|---|---|
| 26 | 3 | | CH$_2$CH$_2$CH$_2$CH$_2$CH$_2$ | 308–312 (dec) | C$_{20}$H$_{23}$Cl$_2$N$_5$O$_2$.HCl | see note 1 | | | 62% | 69% |
| 27 | 3 | CH$_2$CH$_2$CH$_3$ | CH$_2$CH$_2$CH$_3$ | 312–315 (dec) | C$_{21}$H$_{27}$Cl$_2$N$_5$O$_2$.HCl.H$_2$O | 46.76 (46.42 | 5.62 5.75 | 12.64 12.89) | 58% | 88% |
| 28 | 3 | H | C(CH$_3$)$_3$ | >300 | C$_{19}$H$_{23}$Cl$_2$N$_5$O$_2$.2HCl | 45.70 (45.89 | 5.19 5.07 | 13.87 14.08) | 41% | 75% |
| 29 | 3 | CH$_2$CH$_3$ | CH$_2$CH$_3$ | 291–292 | C$_{19}$H$_{23}$Cl$_2$N$_5$O$_2$.HCl.H$_2$O | 47.56 (47.66 | 5.36 5.47 | 14.53 14.63) | 80% | 88% |
| 30 | 3 | | CH$_2$CH$_2$CH$_2$CH$_2$ | 291–292 | C$_{19}$H$_{21}$Cl$_2$N$_5$O$_2$.2HCl.0.25H$_2$O | 45.59 (45.67 | 4.63 4.74 | 13.81 14.01) | 77% | 81% |
| 31 | 3 | H | CH$_2$Ph | >190 (dec) | C$_{22}$H$_{21}$Cl$_2$N$_5$O$_2$.HCl.H$_2$O | 51.51 (51.53 | 4.41 4.72 | 13.40 13.66) | 25% note 2 | 61% |
| 32 | 3 | H | CH$_2$CH$_2$Ph | >190 (dec) | C$_{23}$H$_{23}$Cl$_2$N$_5$O$_2$.HCl.H$_2$O | 52.60 (52.43 | 4.95 4.97 | 12.70 13.29) | 42% | 88% |
| 33 | 3 | CH$_3$ | CH$_3$ | forms glass at 210 | C$_{17}$H$_{19}$Cl$_2$N$_5$O$_2$.HCl.H$_2$O | 44.95 (45.30 | 4.60 4.92 | 15.21 15.54) | 44% note 3 | 66% |
| 34 | 3 | H | H | >190 (dec) | C$_{15}$H$_{15}$Cl$_2$N$_5$O$_2$.HCl | see note 4 | | | 30% note 3 | 50% |
| 35 | 3 | H | c-C$_6$H$_{11}$ | forms glass at 210 | C$_{21}$H$_{25}$Cl$_2$N$_5$O$_2$.2HCl.0.25H$_2$O | 47.68 (47.79 | 5.39 5.25 | 13.23 13.26) | 32% | 60% |
| 36 | 3 | CH$_3$ | c-C$_6$H$_{11}$ | forms glass at 200 | C$_{22}$H$_{27}$Cl$_2$N$_5$O$_2$.HCl.H$_2$O | 50.80 (50.93 | 5.80 5.83 | 13.13 13.50) | 46% | 49% |
| 37 | 3 | H | C(CH$_3$)$_2$CH$_2$CH$_3$ | forms glass at 228 | C$_{20}$H$_{25}$Cl$_2$N$_5$O$_2$.2HCl.H$_2$O | 45.39 (45.39 | 5.51 5.52 | 13.24 13.23) | 11% | 61% |
| 38 | 2 | | CH$_2$CH$_2$OCH$_2$CH$_2$ | >310 | C$_{18}$H$_{19}$Cl$_2$N$_5$O$_3$.2HCl | 43.47 (43.48 | 4.52 4.26 | 13.97 14.09) | 81% | 83% |
| 39 | 2 | CH$_2$CH$_3$ | CH$_2$CH$_3$ | 283–286 | C$_{18}$H$_{21}$Cl$_2$N$_5$O$_2$.2HCl | 44.80 (44.74 | 5.24 4.80 | 14.22 14.49) | 70% | 75% |
| 40 | 2 | H | CH$_2$Ph | 290–295 | C$_{21}$H$_{19}$Cl$_2$N$_5$O$_2$.HCl.H$_2$O | 50.89 (50.57 | 4.24 4.45 | 14.03 14.03) | 59% | 76% |
| 41 | 2 | H | c-C$_6$H$_{11}$ | forms glass at 230 | C$_{20}$H$_{23}$Cl$_2$N$_5$O$_2$.HCl.0.5H$_2$O. 0.6dioxane | 50.90 (50.70 | 5.18 4.90 | 12.90 13.20) | 36% | 45% |
| 42 | 2 | H | CH$_2$(3-pyridyl) | forms glass at 231–233 | C$_{20}$H$_{18}$Cl$_2$N$_6$O$_2$.2HCl.1.25H$_2$O | 44.36 (44.42 | 3.92 4.19 | 15.14 15.54) | 68% | 82% |

Notes to Table 4
1. $^1$H NMR (300 MHz, DMSO-d$_6$) 1.35 (1H, m), 1.73 (3H, m), 1.88 (2H, m), 2.40 (2H, t, J 6 Hz), 2.80 (2H, m), 2.93 (2H, m), 5.67 (2H, s), 7.33 (1H, s), 7.35 (1H, s), 7.60 (1H, s), 978 (1H, s), 11.64 (1H, s), 12.15 (1H, s). m/z (thermospray) 436 (MH$^+$).
2. Reaction at 20° C.
3. Reaction in tetrahydrofuran/dimethylformamide = 1:1 at 20° C.
4. $^1$H NMR (250 MHz, DMSO-d$_6$) 1.72 (2H, m), 2.41 (2H, m), 2.71 (2H, m), 5.63 (2H s), 7.29 (1H, s), 7.34 (1H, s), 7.60 (1H, s), 7.81 (3H, br s), 11.62 (1H, br s), 12.15 (1H, br s). m/z (thermospray) 368 (MH$^+$).

Example 43

1,4-Dihydro-6,7-dichloro-5-{[2-N-(1,1-dimethylpropyl)amino)ethyl]pyrazol-1-ylmethyl}quinoxalin-2,3-dione hydrochloride (a) 4-(2-Chloroethyl)pyrazole hydrochloride (250 mg, 1.0 mmol) was added to a suspension of sodium hydride (90 mg, 80% oil dispersion, 3.0 mmol) in dry tetrahydrofuran (10 mL) at 0° C. under nitrogen with stirring. Immediately 5-bromomethyl-6,7-dichloro-2,3-dimethoxyquinoxaline (352 mg, 1.0 mmol) was added, and the mixture was allowed to warm to 10° C. over 2 hours. The mixture was partitioned between ethyl acetate (50 mL) and water (50 mL). The organic solution was dried (MgSO$_4$) and concentrated under reduced pressure. Purification by flash chromatography (gradient elution with ethyl acetate/hexane), followed by trituration with methanol gave 5-[(2-chloroethyl)pyrazol-1-ylmethyl]-6,7-dichloro-2,3-dimethoxyquinoxaline (254 mg, 63%), as a white solid.

$^1$H NMR (300 MHz, CDCl$_3$) 2.84 (2H, t, J 6 Hz), 3.55 (2H, t, J 6 Hz), 4.10 (3H, s), 4.14 (3H, s), 5.93 (2H, s), 7.30 (1H, s), 7.35 (1H, s), 7.92 (1H, s). m/z (thermospray) 425 (MH$^+$).

(b) A mixture of 5-[(2-chloroethyl)pyrazol-1-ylmethyl]-6,7-dichloro-2,3-dimethoxyquinoxaline (150 mg, 0.37 mmol), 1,1-dimethyl-1-propylamine (3 mL) and ethanol (5 mL) were heated in a closed vessel at 105° C. for 7 hours. The mixture was cooled, the solvent was removed under reduced pressure, and the residue was dissolved in ethyl acetate (75 mL). The solution was washed with saturated aqueous sodium bicarbonate, dried (MgSO$_4$) and concentrated under reduced pressure. Purification by flash chromatography (elution with dichloromethane, then an ethyl acetate/methanol/triethylamine gradient) gave 6,7-dichloro-2,3-dimethoxy-5-{[2-(N-(1,1-dimethylpropyl)amino)ethyl]pyrazol-1-ylmethyl}quinoxaline (65 mg, 38%), as a pale yellow solid.

$^1$H NMR (300 MHz, CDCl$_3$) 0.70 (3H, t, J 6 Hz), 0.98 (6H, s), 1.36 (2H, q, J 6 Hz), 2.64 (4H, m), 4.10 (6H, s), 5.94 (2H, s), 7.19 (1H, s), 7.32 (1H, s), 7.93 (1H, s). m/z (thermospray) 452 (MH$^+$).

(c) A mixure of the product from (b) above, (61 mg, 0.13 mmol), 2M hydrochloric acid (5 mL) and dioxane (5 mL) was heated at reflux for 5 hours. The mixture was concentrated under reduced pressure, diluted with acetone (50 mL) and filtered. The solid was dried under vacuum to give the title compound as an off-white solid (47 mg, 72%), mp >226° C. (forms glass). Found: C, 45.39; H, 5.15; N, 13.99. C$_{19}$H$_{23}$Cl$_2$N$_5$O$_2$.2HCl0.75H$_2$O requires C, 45.26; H, 4.80; N, 13.89%.

$^1$H NMR (300 MHz, DMSO-d$_6$) 0.86 (3H, t, J 6 Hz), 1.20 (6H, s), 1.42 (2H, q, J 6 Hz), 2.75 (2H, m), 2.97 (2H, m), 5.66 (2H, s), 7.36 (1H, s), 7.42 (1H, s), 7.63 (1H, s), 8.42 (1H, br s), 11.70 (1H, br s), 12.10 (1H, br s). m/z (thermospray) 425 (MH$^+$).

Example 44

1,4-Dihydro-6,7-dichloro-5-[5-(N,N-dimethylaminomethyl)-1,2,3-benzotriazol-1-ylmethyl]quinoxalin-2,3-dione A mixture of 6,7-dichloro-2,3-dimethoxy-5-[5-(N,N-dimethylaminomethyl)-1,2,3-benzotriazol-1-ylmethyl]quinoxaline (Preparation 24, 110 mg, 0.25 mmol), 2M hydrochloric acid (10 mL) and dioxane (10 mL) was heated at reflux for 5.5 hours. The mixture was concentrated under reduced pressure, diluted with acetone (10 mL) and filtered. The solid was dried under vacuum to give the title compound as an off-white solid (97 mg, 94%), mp 282° C. Found: C, 45.57; H, 4.00; N, 17.67. C$_{18}$H$_{16}$Cl$_2$N$_6$O$_2$.HCl.H$_2$O requires C, 45.64; H, 4.04; N, 17.74%.

Examples 45–51

The Examples 45–51, shown in Table 5, were prepared by the method of Example 1(b) using the corresponding 5-heterocyclylmethyl quinoxaline derivatives (Preparations 26–32).

TABLE 5

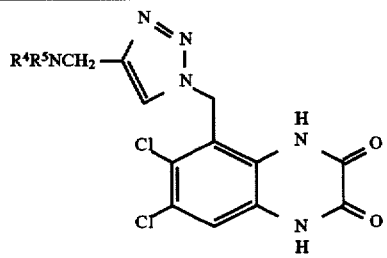

| | | | | | | Analysis: Found (Requires) | | |
|---|---|---|---|---|---|---|---|---|
| Example | R$^4$ | R$^5$ | mp (°C.) | Yield | Formula | C | H | N |
| 45 | CH$_2$CH$_3$ | CH$_2$CH$_3$ | 236 | 96% | C$_{16}$H$_{18}$Cl$_2$N$_6$O$_2$.HCl.H$_2$O | 42.14 (42.54 | 4.66 4.69 | 18.27 18.60) |
| 46 | | CH$_2$CH$_2$CH$_2$CH$_2$CH$_2$ | 289 | 78% | C$_{17}$H$_{18}$Cl$_2$N$_6$O$_2$.HCl.1.25H$_2$O | 43.40 (43.61 | 4.67 4.62 | 18.28 17.94) |
| 47 | H | CH$_2$CH$_2$CH$_2$CH$_3$ | 273 | 91% | C$_{16}$H$_{18}$Cl$_2$N$_6$O$_2$ | $^1$H NMR (300 MHz, DMSO-d$_6$) 0.87 (3H, t, J 7 Hz), 1.31 (2H, m), 1.56 (2H, m), 2.88 (2H, m), 4.17 (2H, s), 6.04 (2H, s), 7.42 (1H, s), 8.24 (1H, s), 9.09 (1H, br s), other NH not observed. m/z (thermospray) 397 (MH$^+$). | | |
| 48 | | CH$_2$CH$_2$CH$_2$CH$_2$CH$_2$CH$_2$ | 285 | 90% | C$_{18}$H$_{20}$Cl$_2$N$_6$O$_2$.HCl.1.33H$_2$O | 44.93 (44.69 | 5.01 4.93 | 17.01 17.37) |
| 49 | | CH$_2$CH$_2$OCH$_2$CH$_2$ | 280 | 93% | C$_{16}$H$_{16}$Cl$_2$N$_6$O$_3$.HCl | $^1$H NMR (300 MHz, DMSO-d$_6$) 3.06 (2H, br s), 3.28 (2H, br s), 3.67 (2H, br s), 3.91 (2H, br s), 6.00 (2H, s), 7.40 (1H, s), 8.33 (1H, s), 10.93 (1H, br s), 11.88 (1H, br s), 12.22 (1H, br s). m/z (thermospray) 424 (MH$^+$). | | |
| 50 | | CH$_2$CH$_2$N(CH$_3$)CH$_2$CH$_2$ | 265 | 79% | C$_{17}$H$_{19}$Cl$_2$N$_7$O$_2$.HCl | $^1$H NMR (300 MHz, DMSO-d$_6$/CF$_3$CO$_2$D) 2.81 (3H, s), 3.65 (4H, br s), 4.52 (2H s), 6.02 (2H, s), 7.40 (1H, s), 8.32 (1H, s). m/z (thermospray) 424 (MH$^+$). | | |
| 51 | H | C(CH$_3$)$_3$ | 270 (dec) | 87% | C$_{16}$H$_{18}$Cl$_2$N$_6$O$_2$.HCl.H$_2$O | 42.46 (42.54 | 4.57 4.69 | 18.90 18.60) |

PREPARATION OF SYNTHETIC INTERMEDIATES

Preparation 1: 5-Bromomethyl-6,7-dichloro-2,3-dimethoxyquinoxaline (a) A solution of 2,4,5-trichloronitrobenzene (103 g, 0.46 mol) and t-butyl chloroacetate (79 mL, 0.55 mol) in dry tetrahydrofuran (400 mL) was added dropwise over 30 minutes to a solution of potassium t-butoxide (128 g, 1.14 mol) in dry tetrahydrofuran (800 mL) with stirring, under nitrogen keeping the temperature at −40° C. After the addition was complete, the resulting dark blue solution was stirred for a further 30 minutes. The mixture was poured into 0.5M hydrochloric acid (2 L) and the product was extracted into ethyl acetate (2.5 L and 1 L). The combined organic solutions were dried (MgSO$_4$) and evaporated onto silica gel (70–200µ, 200 g). The silica gel was applied to the top of a silica gel chromatography column (800 g), and the product was eluted using a hexane/ethyl acetate gradient. Product-containing fractions were combined and evaporated to give a yellow solid, which was triturated with hexane to give t-butyl (2-nitro-3,5,6-trichlorophenyl)acetate (91.8 g, 59%) as a white solid. Found C, 42.32; H, 3.50; N, 4.03. $C_{12}H_{12}Cl_3NO_4$ requires C, 42.32; H, 3.55, N, 4.11%.

$^1$H NMR (300 MHz, CDCl$_3$) 1.42 (9H, s), 3.73 (2H, s), 7.60 (1H, s). m/z (thermospray) 357 (MNH$_4^+$).

(b) A mixture of t-butyl (2-nitro-3,5,6-trichlorophenyl) acetate (123 g, 0.361 mol) and saturated aqueous ammonia (300 mL) in 2-methoxy ethanol (360 mL) was heated in an autoclave at 150° C. for 72 hours. The resulting viscous, black mixture was diluted with water (1 L) and ethyl acetate (1 L) and filtered through Arbocel filter aid. The dark red filtrate was separated, and the aqueous layer extracted with ethyl acetate (2×1 L). The combined organic solutions were washed with brine (1 L), dried (MgSO$_4$) and evaporated onto silica gel (70–200µ, 200 g). The silica gel was applied to the top of a chromatography column containing silica gel (40–60 µ, 800 g). Elution with hexane/ethyl acetate (98:2–92:8) gave 3-amino-5,6-dichloro-2-nitrotoluene (EP-A-0385850) as a bright orange solid (39.7 g), which was contaminated with 5-amino-3,6-dichloro-2-nitrotoluene (14%). This mixture was carried onto the next step without further purification. $^1$H NMR (300 MD, CDCl$_3$) 2.48 (3H, s), 4.80 (2H, s), 6.82 (1H, s).

(c) A solution of sodium dithionite (94 g, 0.54 mol) in water (1 L) was added to a stirred mixture of 3-amino-5,6-dichloro-2-nitrotoluene (39.7 g, 0.18 mol) and potassium bicarbonate (94 g, 0.94 mmol) in methanol (1 L) at room temperature. After 30 minutes, the mixture was concentrated under reduced pressure and the resulting suspension extracted with ethyl acetate (total of 700 mL). The extracts were dried (MgSO$_4$) and concentrated under reduced pressure to give 2,3-diamino-5,6-dichlorotoluene (26.1 g, 38% over 2 steps) as a brown solid. $^1$H NMR (300 MHz, CDCl$_3$) 2.28 (3H, s), 3.36 (2H, br s), 3.42 (2H, br s), 6.72 (1H, s).

(d) A mixture of 2,3-diamino-5,6-dichlorotoluene (21.6 g, 0.137 mol) and oxalic acid (18.45 g, 0.206 mol) in hydrochloric acid (4M, 900 mL) was heated at reflux for 6 hours, cooled and filtered. The dark brown solid was suspended in diethyl ether, filtered and washed with more ether to give 1,4-dihydro-6,7-dichloro-5-methyl-quinoxaline-2,3-dione (22.06 g, 66%). $^1$H NMR (300 MHz, DMSO) 2.40 (3H, s), 7.14 (1H, s), 11.37 (1H, s), 11.94 (1H, s).

(e) A mixture of 1,4dihydro-6,7-dichloro-5-methylquinoxaline-2,3-dione (22.06 g, 90 mmol), thionyl chloride (300 mL) and dimethylformamide (1 mL) was heated at reflux for 3 hours, cooled and poured slowly into iced water. The resulting dark yellow precipitate was filtered off to give 5-methyl-2,3,6,7-tetrachloroquinoxaline (24.42 g, 96%). $^1$H NMR (300 MHz, CDCl$_3$) 2.85 (3H, s), 8.02 (1H, s).

(f) A solution of sodium methoxide (38 mL, 25% solution in methanol, 175 mmol) was added over 10 minutes to a solution of 5-methyl-2,3,6,7-tetrachloroquinoxaline (21 g, 74 mmol) in dry tetrahydrofuran (200 mL) at 20° C. There was a mildly exothermic reaction followed by formation of a precipitate. After 1 hour the mixture was diluted with ethyl acetate (3 L), washed with water (1 L), dried (MgSO$_4$) and concentrated under reduced pressure to give 6,7dichloro-2,3-dimethoxy-5-methylquinoxaline (20.3 g, 100%).

$^1$H NMR (300M, CDCl$_3$) 2.75 (3H, s), 4.15 (3H, s), 4.18 (3H, s), 7.78 (1H, s). m/z (thermospray) 273 (MH$^+$).

(g) A mixture of 6,7-dichloro-2,3-dimethoxy-5-methylquinoxaline (22.0 g, 80.5 mmol), N-bromosucciimide (17.2 g, 96.6 mmol) and α,α'-azoisobutyronitrile (1.3 g, 8.0 mmol) was heated at reflux in 1,1,1-tricloroethane (400 mL) for 4 hours under irradiation from a 500 W sunlamp. The mixture was cooled, silica gel (50 g, 60–230 µ) was added, and the solvent was removed under reduced pressure. The residue was applied to the top of a silica gel chromatography column, and the product was eluted using a hexane/ethyl acetate gradient. The product was trituated with hexane to give 5-bromomethyl-6,7-dichloro-2,3-dimethoxyquinoxaline (25.3 g, 87%) as a fluffy white solid. Found: C, 37.72; H, 2.40; N, 7.40; $C_{11}H_9BrCl_2N_2O_2$ requires C, 37.53; H, 2.58; N, 7.96%. $^1$H NMR (300M, CDCl$_3$) 4.15 (3H, s), 4.22 (3H, s), 5.20 (2H, s), 7.89 (1H, s).

Preparation 2: 6,7-Dichloro-2,3-dimethoxy-5-(1-hydroxyethyl)quinoxaline (a) A mixture of 1,4-dihydro-6,7-dichloro-5-nitroquinoxalin-2,3-dione (WO 94/00124)(84 g, 0.34 mol), thionyl chloride (840 mL) and dimethylformamide (0.5 mL) was heated at reflux for 3 hours, cooled and concentrated under reduced pressure. Ethyl acetate (300 L) was added and removed under reduced pressure, followed by petroleum ether, (b.p. 100°–120° C.). The solid residue was recrystallised from hot petroleum ether (b.p. 100°–120° C.) to give 5-nitro-2,3,6,7-tetrachloroquinoxaline (78 g, 73%) as a light yellow solid. $^1$H NMR (300 MHz, CDCl$_3$) 8.6 (1H, s).

(b) Tin (II) chloride dihydrate (346.3 g, 1.54 mol) was added to a solution of the product from (a) above (96.2 g, 0.31 mol) in ethyl acetate (1.8 L). The mixture was heated under reflux for 4 hours, cooled, and poured cautiously into an excess of aqueous saturated sodium bicarbonate. The mixture was filtered through Celite, washing well with ethyl acetate. The filter cake was macerated with more ethyl acetate and the solid material filtered off. The combined ethyl acetate solutions were dried (MgSO$_4$) and concentrated under reduced pressure to give 5-amino-2,3,6,7-tetrachloroquinoxaline (73.4 g, 84%) as a yellow solid.

$^1$H NMR (300 MHz, CDCl$_3$) 5.45 (2H, br s), 7.47 (1H, s). m/z (thermospray) 385 (MH$^+$).

(c) A solution of sodium methoxide (25% solution in methanol, 274 mL, 1.28 mol) was added to a suspension of 5-amino-2,3,6,7-tetrachloroquinoxaline (72.4 g, 0.256 mol) in dry methanol (1 L) and the resulting mixture was heated at reflux for 30 minutes. The mixture was cooled, concentrated under reduced pressure, and the residue partitioned between water and ethyl acetate (total of 8 L). The organic solution was dried (MgSO$_4$) and concentrated under reduced pressure. The crude product was purified by trituration with methanol, followed by dissolution in dichloromethane (2 L) and filtration. The filtrate was concentrated under reduced pressure to give a yellow solid (55.0 g, 79%).

$^1$H NMR (300 MHz, CDCl$_3$) 4.13 (3H, s), 4.14 (3H, s), 5.07 (2H, br s), 7.26 (1H, s). m/z (thermospray) 274 (MH$^+$).

(d) 5-Amino-6,7-dichloro-2,3-dimethoxyquinoxaline (from (c) above) (38.12 g, 0.14 mol) was dissolved in acetone (2 L) and cooled to 0° C. Whilst being agitated using a mechanical stirrer, the solution was treated first with 2M hydrochloric acid (396 mL, 0.79 mol) and then dropwise with 1M aqueous sodium nitrite (208 mL, 0.208 mol), maintaining the temperature of the mixture at 0° C. After the additions were complete, the mixture was stirred for 15 minutes, then treated with 5M aqueous potassium iodide (278 mL, 1.39 mol) maintaining the temperature below 5° C. The mixture was then allowed to warm to 10° C. over 30 minutes. The acetone was removed under reduced pressure and the residue partitioned between water and ethyl acetate (total of 4 L). The organic solution was washed with 10% aqueous sodium bisulphite, saturated aqueous sodium bicarbonate, dried (MgSO$_4$), and concentrated under reduced pressure. Purification by flash chromatography (eluting with toluene) gave 6,7-dichloro-2,3-dimethoxy-5-iodoquinoxaline (16.9 g, 32%).

$^1$H NMR (300M, CDCl$_3$) 4.17 (3H, s), 4.24 (3H, s), 7.91 (1H, s).

(e) A mixture of 6,7-dichloro-2,3-dimethoxy-5-iodoquinoxaline (3.0 g, 7.8 mmol), tributylvinylstannane (4.94 g, 15.6 mmol), lithium chloride (991 mg, 23.4 mmol) and bis(triphenylphosphine)palladium (II) chloride (600 mg, 1.56 mmol) in dry dimethylformamide (100 mL) was heated at 100° C. for 1.5 hours. The mixture was cooled, filtered, and the filtrate concentrated under reduced pressure. The residue was purified by flash chromatography (eluting with toluene) to give 6,7-dichloro-2,3-dimethoxy-5-ethenylquinoxaline (1.76 g, 79%), as a white solid.

$^1$H NMR (300 MHz, CDCl$_3$) 4.11 (3H, s), 4.14 (3H, s), 5.84 (1H, d, J 12 Hz), 6.33 (1H, d, J 18 Hz), 7.18 (1H, dd, J 12 and 18 Hz), 7.77 (1H, s). m/z (thermospray) 285 (MH$^+$).

(f) A mixture of ozone and oxygen was bubbled gently through a stirred solution of 6,7-dichloro-2,3-dimethoxy-5-ethenylquinoxaline (1.76 g, 6.2 mmol) in chloroform (200 mL) at −60° C. until a blue colour persisted. The solution was purged with nitrogen, and then triphenylphosphine (3.23 g, 12.3 mmol) was added. The mixture was allowed to warm to room temperature and stirred for a further 16 hours. The chloroform was removed under reduced pressure and the residue purified by flash chromatography (eluting with toluene) to give 6,7-dichloro-2,3-dimethoxy-5-formylquinoxaline (1.60 g, 90%) as a fluffy white solid.

$^1$H NMR (300 MF, CDCl$_3$) 4.16 (6H, s), 8.08 (1H, s), 11.06 (1H, s). m/z (thermospray) 287 (MH$^+$).

(g) Methylmagnesium bromide (2.3 mL, 1M in di-n-butylether, 2.3 mmol) was added to a suspension of 6,7-dichloro-2,3-dimethoxy-5-formylquinoxaline (600 mg, 2.09 mmol) in dry tetrahydrofuran (30 mL) under nitrogen at room temperature. After 30 minutes, saturated ammonium chloride (20 mL) was added, and the product was extracted into ethyl acetate (2×30 mL). The combined extracts were dried (MgSO$_4$) and concentrated under reduced pressure to give 6,7-dichloro-2,3-dimethoxy-5-(1-hydroxyethyl) quinoxaline (577 mg, 91%), as a creamy coloured solid.

$^1$H NMR (300 CDCl$_3$) 1.68 (3H, d, J 7 Hz), 4.15 (6H, s), 5.63 (1H, dq, J 7 and 11 Hz), 5.95 (1H, d, J 11 Hz), 7.84 (1H, s). m/z (thermospray) 303 (MH$^+$).

Preparation 3: 5-Chloromethyl-2,3-dimethoxy-6,7-dimethylquinoxaline (a) Silver sulphate (103 g, 0.33 mol) was added over 5 minutes to a stirred suspension of 4,5-dimethyl-2-nitroaniline (50.0 g, 0.30 mol) in ethanol (1500 mL) at 20° C. Iodine (84.0 g, 0.33 mol) was added in portions, and the resulting mixture was stirred for 30 minutes at 20° C. The mixture was filtered, and the filter cake washed thoroughly with ethanol (1 L) and dichloromethane (1 L). The filtrate was concentrated under reduced pressure, and the residue was redissolved in dichloromethane (500 mL), and washed with 10% aqueous sodium metabisulphite (2×500 mL), and brine (250 mL). The solution was dried (MgSO$_4$) and concentrated under reduced pressure to give 4,5-dimethyl-6-iodo-2-nitroaniline (82.1 g, 93%) as an orange solid.

$^1$H NMR (300 MHz, CDCl$_3$) 2.32 (3H, s), 2.51 (3H, s), 6.75 (2H, br s), 7.97 (1H, s). m/z (thermospray) 310 (MNH$_4^+$).

(b) A mixture of 4,5-dimethyl-6-iodo-2-nitroaniline (17.52 g, 60 mmol), bis(triphenylphosphine)palladium (II) chloride (1.75 g) and ethyldiisopropylamine (11.5 mL, 66 mmol) in tetrahydofuran/methanol (1:1, 300 mL) was heated at 100° C. under a carbon monoxide atmosphere (100 psi, 6.7 atm) in an autoclave for 8 hours. After being cooled, the mixture was concentrated under reduced pressure, and the residue was partitioned between dichloromethane (150 mL) and water (150 mL). The aqueous layer was extracted with dichloromethane (2×150 mL), and the combined extracts were dried (MgSO$_4$) and concentrated under reduced pressure. Purification by flash chromatography, eluting with hexane:ethyl acetate (9:1), then (3:1) and finally hexane:dichloromethane (1:1) gave methyl 2-amino-5,6-dimethyl-3-nitrobenzoate (12.94 g, 96%) as an orange solid.

$^1$H NMR (300 MHz, CDCl$_3$) 2.23 (3H, s), 2.29 (3H, s), 3.97 (3H, s), 7.00 (2H, br s), 8.05 (1H, s). m/z (thermospray) 225 (MH$^+$).

(c) A solution of methyl 2-amino-5,6-dimethyl-3-nitrobenzoate (11.78 g, 52.5 mmol) in dichloromethane (525 mL) was hydrogenated over 10% palladium on charcoal (1.2 g) at 50 psi (3.3 atm) and 50° C. for 16 hours. Another portion of catalyst (1.2 g) was added, and hydrogenation was allowed to proceed for a further 16 hours. The mixture was filtered through Arbocel filter aid, and the filtrate was concentrated under reduced pressure. The residue was purified by flash chromatography (gradient elution with dichloromethane/methanol) to give methyl 2,3-diamino-5,6-dimethylbenzoate (8.36 g, 82%) as an orange oil.

$^1$H NMR (300 MHz, CDCl$_3$) 2.14 (3H, s), 2.18 (3H, s), 3.24 (2H, br s), 3.90 (3H, s), 4.20 (2H, br s), 6.60 (1H, s). m/z (thermospray) 195 (MH$^+$).

(d) A mixture of methyl 2,3-diamino-5,6-dimethylbenzoate (8.33 g, 42.9 mmol), oxalic acid (5.4 g, 60.0 mmol), and 4M hydrochloric acid (400 mL) was heated at reflux under nitrogen for 4 hours. After being cooled, the solid which had formed was filtered off, washed with water, and dried under vacum to give a 1,4-dihydro-6,7-dimethoxy-5-(methoxycarbonyl)quinoxaline-2,3-dione (10.03 g, 94%) as a cream-coloured solid, mp >300° C. Found: C, 58.03; H, 4.73; N, 11.02; C$_{12}$H$_{12}$N$_2$O$_4$ requires C, 58.06; H, 4.87; N 11.29%.

$^1$H NMR (300 MHz, DMSO-d$_6$) 2.10 (3H, s), 2.20 (3H, s), 3.89 (3H, s), 7.00 (1H, s), 11.32 (1H, br s), 11.90 (1H, br s).

(e) A mixture of 1,4-dihydro-6,7-dimethoxy-5-(methoxycarbonyl)quinoxaline (10.0 g, 40.3 mmol), thionyl chloride (100 mL) and dimethylformamide (1 mL) was heated under nitrogen at reflux for 6 hours. After being cooled, the mixture was concentrated under reduced pressure, dissolved in dichloromethane and washed with water. The solution was dried (MgSO$_4$) and concentrated under reduced pressure. The residue was purified by flash chromatography (eluting with dichloromethane) to give 2,3- dichloro-6,7-dimethyl-5-(methoxycarbonyl)quinoxaline (9.8 g, 85%) as a pale yellow solid.

¹H NMR (300 MHz, CDCl₃) 2.44 (3H, s), 2.52 (3H, s), 4.05 (3H, s), 7.82 (1H, s). m/z (thermospray) 285 (MH⁺).

(f) Sodium hydride (2.2 g, 80% dispersion in oil, 73.4 mmol) was added in portions to a stirred solution of 2,3-dichloro-6,7-dimethyl-5-(methoxycarbonyl)quinoxaline (9.8 g, 34.4 mmol) in dry methanol (300 mL) under nitrogen at 20° C. After 16 hours, the solvent was removed under reduced pressure, and the residue was partitioned between dichloromethane and water. The organic solution was dried (MgSO₄), and concentrated under reduced pressure to give 2,3-dimethoxy-6,7-dimethyl-5-(methoxycarbonyl) quinoxaline (8.6 g, 91%) as a pale yellow solid.

¹H NMR (300 MH, CDCl₃) 2.34 (3H, s), 2.40 (3H, s), 4.02 (3H, s), 4.07 (3H, s), 4.11 (3H, s), 7.60 (1H, s). m/z (thermospray) 277 (MH⁺).

(g) Diisobutylaluminium hydride (19.9 mL, 1M in dichloromethane, 19.9 mmol) was added dropwise over 30 minutes to a stirred solution of 2,3-dimethoxy-6,7-dimethyl-5-(methoxycarbonyl)quinoxaline (5.0 g, 18.1 mmol) in dry dichloromethane (300 mL) under nitrogen at −90° C. After 1 hour, another portion of diisobutylaluminium hydride (19.9 mL) was added, and the mixture was stirred for a further 1.5 hours. Saturated aqueous ammonium chloride (100 mL) was added, and the mixture was allow to warm to room temperature. The mixture was filtered through Arbocel filter aid, and the filtrate was washed thoroughly with dichloromethane. The aqueous layer was separated and extracted with two portions of dichloromethane. The combined organic solutions were dried (MgSO₄) and concentrated under reduced pressure. The residue was purified by flash chromatography to give 2,3-dimethoxy-6,7-dimethyl-5-hydroxymethyl quinoxaline (1.25 g, 28%).

¹H NMR (300MHz, CDCl₃) 2.56 (6H, s), 3.57 (1H, br s) 4.14 (6H, s), 5.23 (2H, s), 7.55 (1H, s). m/z (thermospray) 249 (MH⁺).

(h) Thionyl chloride (0.44 mL, 6.0 mmol) was added dropwise to a solution of 2,3-dimethoxy-6,7-dimethyl-5-hydroxymethylquinoxaline (0.50 g, 2.0 mmol) in toluene (30 mL) and pyridine (0.81 mL, 10.0 mmol) under nitrogen at 5° C. After 20 minutes, water (20 mL), and the aqueous layer was extracted with ethyl acetate (2×20 mL). The combined organic solutions were washed with 2M hydrochloric acid, dried (MgSO₄) and concentrated under reduced pressure. Purification of the residue by flash chromatography (eluting with dichloromethane) gave 5-(chloromethyl)-2,3-dimethoxy-6,7-dimethylquinoxaline (0.18 g, 34%) as a pale yellow solid.

¹H NMR (300 MHz, CDCl₃) 2.45 (3H, s), 2.50 (3H, s), 4.15 (3H, s), 4.19 (3H, s), 5.31 (2H, s), 7.60 (1H, s). m/z (thermospray) 267 (MH⁺).

Preparation 4: 5-(1-Bromoethyl)-6,7-dichloro-2,3-dimethoxyquinoxaline

Carbon tetrabromide (832 mg, 2.51 mmol) was added in portions to a solution of 6,7-dichloro-2,3-dimethoxy-5-(1-hydroxyethyl)quinoxaline (380 mg, 1.25 mmol) (Preparation 2) and triphenylphosphine (658 mg, 2.51 mmol) in dry dichloromethane (20 mL) at 20 C. The mixture was stirred for 48 hours, and the solvent was removed under reduced pressure. Purification by flash chromatography eluting with hexane/dichloromethane (1:1) gave the title compound (362 mg, 70%), as a white solid.

¹H NMR (300 MHz, CDCl₃) rotational isomers evident: 2.26 (3H, d, J 7 Hz, CH₃ minor rotamer), 2.42 (3H, d, J 7 Hz, CH₃ major rotamer), 4.16 (3H, s, CH₃O, both rotamers), 4.23 (3H, s, CH₃O, minor rotamer), 4.26 (3H, s, CH₃O, major rotamer), 6.17 (1H, q, J 7 Hz, CHCH₃ major rotamer), 6.97 (1H, q, J 7 Hz, CHCH₃ minor rotamer), 7.91 (1H, s, aromatic H both rotamers). m/z (thermospray) 366 (MH⁺).

Preparation 5: 5-(1-Bromopropyl)-6,7-dichloro-2,3-dimethoxyquinoxaline (a) Ethylmagnesium bromide (9.08 mL, 3M in diethyl ether) was added to a suspension of 6,7dichloro-2,3-dimethoxy-5-formylquinoxaline (3.91 g, 13.62 mmol) (Preparation 2) in dry tetrahydrofuran (200 mL) under nitrogen at room temperature. After 30 minutes, saturated sodium chloride (50 mL) was added, and the product was extracted into ethyl acetate (2×100 mL). The combined extracts were dried (MgSO₄) and concentrated under reduced pressure. Purification by flash chromatography (eluting with dichloromethane) gave 6,7-dichloro-2,3-dimethoxy-5-(1-hydroxypropyl)-quinoxaline (1.86 g, 43%), as a pale yellow solid.

¹H NMR (300 MHz, CDCl₃) 1.05 (3H, t, J 7 Hz), 1.99 (2H, m), 4.11 (3H, s), 4.12 (3H, s), 5.40 (1H, m), 5.65 (1H, d, J 11 Hz), 7.81 (1H, s).

(b) 6,7-Dichloro-2,3-dimethoxy-5-(1-hydroxypropyl) quinoxaline was treated with carbon tetrabromide and triphenylphosphine according to the method of Preparation 4 to give the title compound (46% yield) as a white solid.

¹H NMR (300 MHz, CDCl₃) rotational isomers evident: 0.96 (3H, t, J 7 Hz, CH₃ both rotamers), 2.60 (2H, m, CH₂ minor rotamer), 2.80 (2H, m, CH₂ major rotamer), 4.13 (3H, s, CH₃O, both rotamers), 4.18 (3H, s, CH₃O, minor rotamer), 4.20 (3H, s, CH₃O, major rotamer), 5.87 (1H, t, J 7 Hz, CH major rotamer), 6.68 (1H, t , J 7 Hz, CH minor rotamer), 7.87 (1H, s, aromatic H both rotamers). m/z (thermospray) 379 (MH⁺).

Preparation 6: 4-[3-(4-Morpholinyl)propyl]pyrazole hydrochloride

A mixture of 4-(3-chloropropyl)pyrazole hydrochloride (R. G. Jones, M. J. Mann, J. Amer. Chem. Soc., (1953), 75, 4048–4052) (1.80 g, 10 mmol), morpholine (6 mL) and ethanol (9 mL) was heated in a sealed vessel at 105° C. for 18 hours. After being cooled, the volatiles were removed under reduced pressure. The residue was treated with toluene and filtered. The filtrate was concentrated under reduced pressure, dissolved in ethanol (10 mL) and treated with a solution of hydrogen chloride in diethyl ether (1M, 20 mL) at 20° C. The solid which formed was filtered off and dried under vacuum to give the title compound (1.91 g, 70%), as a fawn solid. Found, C, 44.17; H, 6.97; N, 15.05. $C_{10}H_{17}N_3O.2HCl.0.25H_2O$ requires C, 44.05; H, 7.21; N, 15.41%.

¹H NMR (300 MHz, DMSO-d₆) 1.98 (2H, m), 2.40 (2H, m), 3.00 (4H, m), 3.40 (2H, m), 3.80 (4H, m), 7.60 (2H, m), 11.20 (1H, s). m/z (thermospray) 196 (MH⁺).

Preparations 7–23: The compounds in Table 5 below were prepared by the method of Preparation 6, using the appropriate amine in place of morpholine, and 4-(2-chloroethyl) pyrazole hydrochloride (R. G. Jones, M. J. Mann, J. Amer. Chem. Soc., (1953), 75, 4048–4052) in place of 4-(3-chloropropyl)pyrazole hydrochloride, as appropriate.

TABLE 6 structure: pyrazole with N-N-H and (CH₂)ₙNR⁴R⁵ substituent

| Preparation | n | R¹ | R² | Formula | C | H | N | Yield |
|---|---|---|---|---|---|---|---|---|
| 7 | 3 | | CH₂CH₂CH₂CH₂CH₂ | C₁₁H₁₉N₃.2HCl.0.25H₂O | 49.17 (48.80) | 8.06 8.01 | 15.41 15.52) | 72% |
| 8 | 3 | CH₂CH₂CH₃ | CH₂CH₂CH₃ | C₁₂H₂₃N₃.2HCl.0.25H₂O | 50.09 (50.26) | 8.78 8.96 | 14.53 14.65) | 69% |
| 9 | 3 | H | C(CH₃)₃ | C₁₀H₁₉N₃ (note 1) | 1.06 (9H, s), 1.63 (2H, m), 2.50 (2H, t, J 6 Hz), 2.65 (2H, t, J 6 Hz), 7.38 (2H, s). | | | 40% |
| 10 | 3 | CH₂CH₃ | CH₂CH₃ | C₁₀H₁₉N₃.2HCl | 1.16 (6H, t, J 7 Hz), 1.90 (2H, m), 2.87 (4H, m), 3.06 (4H, m), 7.60 (2H, s), 10.4 (1H, br s). | | | note 2 |
| 11 | 3 | | CH₂CH₂CH₂CH₂ | C₁₀H₁₇N₃.2HCl.0.25H₂O | 46.92 (46.79) | 7.91 7.66 | 16.30 16.37) | 56% |
| 12 | 3 | H | CH₂Ph | C₁₃H₁₇N₃.2HCl | 1.90 (2H, m), 2.50 (2H, m), 2.87 (2H, m), 4.11 (2H, m), 7.40 (3H, m), 7.45 (2H, br s), 7.53 (2H, m), 9.20 (2H, br s), 12.57 (1H, br s). | | | 40% |
| 13 | 3 | H | CH₂CH₂Ph | C₁₄H₁₉N₃.2HCl | 55.33 (55.62) | 7.15 6.95 | 13.92 13.90) | 80% |
| 14 | 3 | CH₃ | CH₃ | C₈H₁₅N₃.2HCl | 1.97 (2H, m), 2.51 (2H, m), 2.70 (6H, s), 2.98 (2H, m), 6.16 (2H, br s), 7.87 (2H, s), 10.94 (1H, br s). | | | 89% |
| 15 | 3 | H | H | C₆H₁₁N₃.2HCl | prepared according to method of R. G. Jones, M. J. Mann, J. Amer. Chem. Soc., (1953), 75, 4048–4052 | | | |
| 16 | 3 | H | c-C₆H₁₁ | C₁₂H₂₁N₃.2HCl | 51.20 (51.43) | 8.64 8.27 | 15.04 14.99) | 62% |
| 17 | 3 | CH₃ | c-C₆H₁₁ | C₁₃H₂₃N₃ notes 1 and 3 | 1.05 (5H, m), 1.42 (1H, m), 1.75 (6H, m), 2.25 (3H, s), 2.38 (1H, m), 2.50 (4H, m), 7.40 (2H, s), 10.40 (1H, br s). | | | 50% |
| 18 | 3 | H | C(CH₃)₂CH₂CH₃ | C₁₁H₂₁N₃.2HCl | 0.87 (3H, t, J 7 Hz), 1.19 (6H, s), 1.58 (2H, q, J 7 Hz), 1.97 (2H, m), 2.57 (2H, m), 3.66 (2H, t, 6 Hz), 7.70 (2H, s), 8.03 (3H, br s). | | | 67% |
| 19 | 2 | | CH₂CH₂OCH₂CH₂ | C₉H₁₅N₃O.2HCl | 2.87 (2H, m), 3.08 (2H, m), 3.25 (2H, m), 3.40 (2H, m), 3.82 (2H, m), 3.92 (2H, m), 7.60 (2H, s), 11.30 (1H, s) | | | 90% |
| 20 | 2 | CH₂CH₃ | CH₂CH₃ | C₉H₁₇N₃.2HCl | 44.81 (45.01) | 8.24 7.97 | 17.10 17.50) | 41% |
| 21 | 2 | H | CH₂Ph | C₁₂H₁₅N₃.2HCl.0.25H₂O | 51.82 (51.72) | 6.39 6.33 | 14.94 15.08) | 80% |
| 22 | 2 | H | c-C₆H₁₁ | C₁₁H₁₉N₃.HCl | 1.02–1.39 (5H, m), 1.58 (1H, m), 1.71 (2H, m), 2.03 (2H, m), 2.83 (2H, m), 2.98 (3H, m), 7.58 (2H, s), 8.82 (2H, br s). | | | 83% |
| 23 | 2 | H | CH₂(3-pyridyl) | C₁₁H₁₄N₄.2HCl | 2.74 (2H, m), 3.13 (2H, m), 4.33 (2H, s), 7.60 (2H, s), 7.92 (1H, m), 8.56 (1H, d, J 8 Hz), 8.86 (1H, d, J 5 Hz), 9.03 (1H, s), 9.83 (2H, br s). | | | 51% |

Notes to Table 5. NMR spectra of hydrochloride salts in DMSO-d₆; free bases in CDCl₃.
1) Isolated as the free base.
2) Product contaminated with diethylamine hydrochloride. Used directly in next step without purification.
3) Purified by flash chromatography Preparation 24: 6,7-Dichloro-2,3-dimethoxy-5-[5-(N,N-dimethylaminomethyl)-1,2,3-benzotriazol-1-yl]quioxaline (a) A mixture of 5-chloromethyl-1H-1,2,3-benzotriazole (Synth. Commun., (1993), 23, 2019) (1.34 g, 8.0 mmol) and dimethylamine (33% solution in ethanol, 10 mL) was heated in an autoclave at 100° C. for 12 hours. The solvent was removed under reduced pressure, and the residue was dissolved in saturated aqueous sodium bicarbonate. A continuous extraction using ethyl acetate was performed, and the resulting solution of the product was dried (MgSO₄) and concentrated under reduced pressure to give 5-(N,N-dimethylaminomethyl)-1H-1,2,3-benzotriazole (890 mg, 63%) as a brown hygroscopic gum.

¹H NMR (300 MHz, DMSO-d₆) 2.68 (6H, s), 4.44 (2H, s), 7.65 (1H, br s), 7.96 (1H, br s), 8.15 (1H br s), 10.77 (1H, br s). m/z (thermospray) 177 (MH⁺).

(b) 5-(N,N-Dimethylaminomethyl)-1H-1,2,3-benzotriazole hydrochloride (383 mg 1.8 mmol) was added to a suspension of sodium hydride (108 mg, 80% dispersion in oil, 3.6 mmol) in dry dimethylformamide (20 mL) at room temperature and stirred for 15 minutes. The mixure was cooled to −30° C., 5-bromomethyl-6,7-dichloro-2,3-dimethoxy quinoxaline (Preparation 1, 528 mg, 1.5 mmol) was added, and the mixture was stirred at −30° C. for 1 hour, and then allowed to warm slowly to 0° C. Saturated aqueous ammonium chloride (5 mL) was added, followed by water (50 mL). The product was extracted into ethyl acetate, the extracts were washed with water, dried (MgSO₄) and concentrated under reduced pressure. The residue was purified by flash chromatography (gradient elution with hexane/ethyl acetate, then ethyl acetate/methanol) to give 6,7-dichloro-2,3-dimethoxy-5-[5-(N,N-dimethylaminomethyl)-1,2,3-benzotriazol-1-yl] methylquinoxaline (135 mg, 28%), R_f=0.4 (silica gel, ethyl acetate/methanol=4:1), as the slowest eluted product isomer.

¹H NMR (300 MHz, CDCl₃) 2.23 (6H, s), 3.52 (2H, s), 4.05 (3H, s), 4.13 (3H, s), 6.47 (2H, s), 7.33 (1H, d, J 8 Hz), 7.39 (1H, d, J 8 Hz), 7.86 (1H, s), 7.97 (1H, s). m/z (thermospray) 447 (MH⁺).

The structure of the product was confirmed as the 5-dimethylaminomethylbenzotriazole isomer by Rotating Frame Overhauser Enhancement Spectroscopy.

Preparation 25: 6,7-Dichloro-2,3-dimethoxy-5-[(4-formyl-1,2,3-triazol-1-yl)methyl]quinoxaline (a) A mixture of 5-bromomethyl-6,7-dichloro-2,3-dimethoxyquinoxaline Preparation 1, 2.11 g, 6.00 mmol), methyl 1,2,3-triole-4-carboxylate (J. Org. Chem., (1976), 41, 1041) (1.07 g, 8.4 mmol) and anhydrous potassium carbonate (1.66 g, 12 mmol) in dry tetrahydrofuran (25 mL) was heated at reflux for 18 hours, cooled, poured into water and the solid filtered off. Purification of the solid by flash chromatography (gradient elution with hexane/dichloromethane) gave 6,7-dichloro-2,3-dimethoxy-5-[(4-methoxycarbonyl-1,2,3-triazol-1-yl)methyl]quinoxaline (1.278 g, 54%), R$_f$=0.3 (silica gel, hexane:ethyl acetate= 1:1), as the slowest eluted of the three product isomers.

¹H NMR (300 MHz, CDCl₃) 3.90 (3H, s), 4.11 (3H, s), 4.15 (3H, s), 6.29 (2H, s), 7.93 (1H, s), 8.00 (1H, s). m/z (thermospray) 398 (MH⁺).

(b) A solution of diisobutylaluminium hydride (1M in dichloromethane, 9 mL, 9 mmol) was added dropwise to a stirred suspension of 6,7-dichloro-2,3-dimethoxy-5-[(4-methoxycarbonyl-1,2,3-triazol-1-yl)methyl]quinoxaline (1.087 g, 2.73 mmol) under nitrogen at −78° C. After 2.25 hours, methanol (5 mL) was added, followed by saturated aqueous ammonium chloride (25 mL) 5 minutes later. The mixture was allowed to warm to room temperature, filtered through Arbocel filter aid, washing the filter cake with dichloromethane. The organic solution was dried (MgSO₄) and concentrated under reduced pressure to give 6,7-dichloro-2,3-dimethoxy-5 [(4-formyl-1,2,3-triazol-1-yl) methyl]quinoxaline (981 mg, 98%), as a white solid.

¹H NMR (300 MHz, CDCl₃) 4.13 (3H, s), 4.15 (3H, s), 6.30 (2H, s), 7.99 (1H, s), 8.0 (1H, s), 10.08 (1H, s). m/z (thermospray) 370 (MH⁺).

Preparation 26: 5-[(4-n-Butylaminomethyl-1,2,3-triazol-1-yl)methyl]-6,7-dichloro-2,3-dimethoxyquinoxaline A mixture of 6,7-dichloro-2,3-dimethoxy-5-[4-formyl-1,2,3-triazol-1-yl) methyl]quinoxaline (Preparation 25, 250 mg, 0.68 mmol), n-butylamine (200 μL, 2.04 mmol) and anhydrous magnesium sulphate (270 mg) in dry dichloromethane (10 mL) was stirred at 20° C. for 24 h. The mixture was filtered, concentrated under reduced pressure, and suspended in dry ethanol (50 mL). Sodium borohydride (39 mg, 1.02 mmol) was added, and the mixture was stirred at 20° C. for 30 min. The solvent was removed under reduced pressure, the residue was dissolved in dichloromethane and washed with saturated aqueous sodium bicarbonate. The solution was dried (MgSO₄), concentrated under reduced pressure, and the residue was purified by flash chromatography (gradient elution with ethyl acetate/methanol) to afford the title compound (152 mg, 53%).

¹H NMR (300 MHz, CDCl₃) 0.87 (3H, t, J 7 Hz), 1.29 (2H, m), 1.45 (2H, m), 1.92 (1H, br s), 2.63 (2H, t, J 7 Hz), 3.84 (2H, s), 4.15 (6H, s), 6.22 (2H, s), 7.39 (1H, s), 7.95 (1H, s).

Preparation 27: 5-4-t-Butylaminomethyl-1,2,3-triazol-1-yl-methyl]-6,7-dichloro-2,3-dimethoxy quinoxaline was prepared by the method of Preparation 26, using t-butylamine instead of n-butylamine to give the title compound as a white solid (46%).

¹H NMR (300 MHz, CDCl₃) 1.13 (9H, s), 3.60 (2H, s), 4.15 (3H, s), 4.16 (3H, s), 6.22 (2H, s), 7.40 (1H, s), 7.97 (1H, s). m/z (thermospray) 425 (MH⁺).

Preparation 28: 6,7-Dichloro-2,3-dimethoxy-5-{[4-(1-piperidinylmethyl)-1,2,3-triazol-1-yl]methyl}quinoxaline Sodium triacetoxyborohydride (131 mg, 0.62 mmol) was added to a solution of 6,7-dichloro-2,3-dimethoxy-5-[4-formyl-1,2,3-triazol-1-yl) methyl]quinoxaline (Preparation 25, 250 mg, 0.41 mmol), piperidine (49 μL, 0.49 mmol) and acetic acid (24 μL, 0.41 mmol) in dry tetrahydrofuran (3 mL) at room temperature, with stirring. After 2 hours, the solution was diluted with dichloromethane, washed with saturated aqueous sodium bicarbonate, dried (MgSO₄), and concentrated under reduced pressure. The residue was purified by flash chromatography (gradient elution with ethyl acetate/methanol) to give the title compound (132 mg, 74%) as a white solid.

¹H NMR (300 MHz, CDCl₃) 1.41 (2H, m), 1.55 (4H, m), 2.42 (4H, m), 3.57 (2H, s), 4.14 (6H, s), 6.19 (2H, s), 7.42 (1H, s), 7.97 (1H, s). m/z (thermospray) 439 (MH⁺).

Preparations 29–32: The following compounds shown in Table 6 were prepared by the method of Preparation 28, using 6,7-dichloro-2,3-dimethoxy-5-[4-formyl-1,2,3-triazol-1-yl)methyl]quinoxaline (Preparation 25) and the appropriate amine in place of piperidine.

TABLE 7

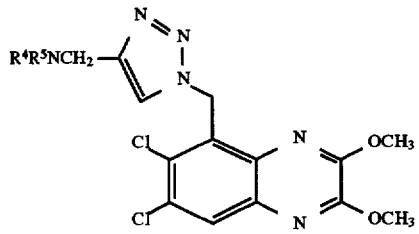

| Preparation | R⁴ | R⁵ | Yield | Formula | Spectroscopic data ¹H NMR (300 MHz, CDCl₃ unless indicated otherwise); MS (thermospray) |
|---|---|---|---|---|---|
| 29 | CH₂CH₃ | CH₂CH₃ | 74% | C₁₈H₂₂Cl₂N₆O₂ | δ$_H$ 1.02 (6H, t, J 7 Hz), 2.49 (4H, q, J 7 Hz), 3.69 (2H, s), 4.15 (6H s), 6.23 (2H, s), 7.35 (1H, s), 7.96 (1H, s). m/z 425 (MH⁺). |
| 30 | CH₂CH₂CH₂CH₂CH₂CH₂ | | 71% | C₂₀H₂₄Cl₂N₆O₂ | δ$_H$ (DMSO-d₆) 1.49 (8H, br s), |

TABLE 7-continued

![structure]

| Preparation | R⁴ | R⁵ | Yield | Formula | Spectroscopic data $^1$H NMR (300 MHz, CDCl$_3$ unless indicated otherwise); MS (thermospray) |
|---|---|---|---|---|---|
|  |  |  |  |  | 2.56 (2H, br s), 3.65 (2H, br s), 4.05 (6H, s), 6.13 (2H, s), 7.93 (1H, br s), 8.07 (1H, s). m/z 451 (MH⁺). |
| 31 | CH$_2$CH$_2$OCH$_2$CH$_2$ |  | 74% | C$_{18}$H$_{20}$Cl$_2$N$_6$O$_3$ | δ$_H$ 2.45 (4H, m), 3.59 (2H s), 3.68 (4H, m), 4.15 (6H, s), 6.24 (2H, s), 7.40 (1H, s), 7.98 (1H, s). m/z (thermospray) 439 (MH⁺). |
| 32 | CH$_2$CH$_2$N(CH$_3$)CH$_2$CH$_2$ |  | 55% | C$_{19}$H$_{23}$Cl$_2$N$_7$O$_2$ | δ$_H$ 2.35 (3H, s), 2.60 (8H, br s), 3.65 (2H, s), 4.15 (6H, s), 6.23 (2H, s), 7.44 (1H, br s), 7.97 (1H, s). m/z (thermospray) 452 (MH⁺). |

We claim:

1. A compound having the formula:

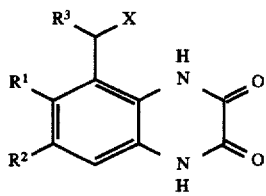

or a pharmaceutically acceptable salt thereof,
wherein R$^1$ and R$^2$ are each independently Cl, Br, CH$_3$, CH$_2$CH$_3$ or CF$_3$;
R$^3$ is H, CH$_3$ or CH$_2$CH$_3$;
and X is a 5-membered heteroaromatic group having up to four nitrogen atoms in the heteroaromatic ring, with each group being directly attached via a ring-nitrogen atom, the group being optionally substituted by C$_1$-C$_6$ alkyl or (CH$_2$)$_n$ NR$^4$R$^5$, wherein n is an integer from 1 to 5 and R$^4$ and R$^5$ are independently H, C$_1$-C$_6$ alkyl, C$_3$-C$_6$ cycloalkyl or C$_1$-C$_4$ alkyl substituted by phenyl or pyridyl, or R$^4$ and R$^5$ are linked to form, together with the nitrogen atom which they are attached a pyrrolidine, piperidine, piperazine, N-(C$_1$-C$_4$ alkyl) piperazine, morpholine or azepine group, or, when X is triazolyl, said group may optionally be benzofused.

2. A compound as claimed in claim 1 wherein R$^1$ and R$^2$ are both Cl.

3. A compound as claimed in claim 1 wherein R$^3$ is CH$_2$CH$_3$.

4. A compound as claimed in claim 1 wherein 3× is 1,2,3-triazol-1-yl, benzotriazol-1-yl or 1,2,4-triazol-4-yl.

5. A compound as claimed in claim 1 wherein X is imidazolyl, pyrazolyl, 1,2,4-triazolyl, tetrazolyl, 1,2,3-triazolyl or benzotriazolyl.

6. A pharmaceutical composition comprising a compound of the formula (I), or a pharmaceutically acceptable salt thereof, as claimed according to claim 1, together with a pharmaceutically acceptable diluent or carrier.

7. The method of treating stroke, transient ischaemic attack, peri-operative ischaemia and traumatic head injury to the brain or spinal cord in an animal subject, which comprises administering to said subject a therapeutically-effective amount of a compound of the formula (I), or a pharmaceutically salt thereof, as claimed in claim 1.

* * * * *